(12) United States Patent
Cunningham

(10) Patent No.: US 11,612,374 B2
(45) Date of Patent: Mar. 28, 2023

(54) SELF-AUSCULTATION DEVICE AND METHOD

(71) Applicant: Randy Mark Cunningham, Roseville, CA (US)

(72) Inventor: Randy Mark Cunningham, Roseville, CA (US)

( * ) Notice: Subject to any disclaimer, the term of this patent is extended or adjusted under 35 U.S.C. 154(b) by 0 days.

(21) Appl. No.: 17/673,700

(22) Filed: Feb. 16, 2022

(65) Prior Publication Data
US 2022/0167942 A1 Jun. 2, 2022

Related U.S. Application Data

(63) Continuation of application No. 17/313,966, filed on May 6, 2021, now Pat. No. 11,266,371.

(60) Provisional application No. 63/021,581, filed on May 7, 2020.

(51) Int. Cl.
| | |
|---|---|
| *A61B 7/02* | (2006.01) |
| *A61B 90/98* | (2016.01) |
| *A61B 7/04* | (2006.01) |
| *H04R 1/46* | (2006.01) |
| *G10L 25/66* | (2013.01) |
| *H04R 1/10* | (2006.01) |
| *G16H 40/63* | (2018.01) |
| *G16H 50/30* | (2018.01) |
| *H04R 3/04* | (2006.01) |
| *A61B 5/0205* | (2006.01) |
| *G06F 3/16* | (2006.01) |

(52) U.S. Cl.
CPC .................. *A61B 7/02* (2013.01); *A61B 7/04* (2013.01); *A61B 90/98* (2016.02); *G10L 25/66* (2013.01); *G16H 40/63* (2018.01); *G16H 50/30* (2018.01); *H04R 1/1041* (2013.01); *H04R 1/46* (2013.01); *H04R 3/04* (2013.01); *A61B 5/0205* (2013.01); *G06F 3/162* (2013.01); *H04R 1/1025* (2013.01); *H04R 2420/07* (2013.01)

(58) Field of Classification Search
CPC .. A61B 7/02; A61B 60/98; A61B 7/04; A61B 5/0205; G16H 50/30; G16H 40/63; G10L 25/66; H04R 1/1041; H04R 1/46; H04R 3/04; H04R 1/1025; H04R 2420/07; G06F 3/162
See application file for complete search history.

(56) References Cited

U.S. PATENT DOCUMENTS 9,770,224 B2 * 9/2017 Park ........................ A61B 7/02

* cited by examiner

*Primary Examiner* — Andrew L Sniezek
(74) *Attorney, Agent, or Firm* — Womble Bond Dickinson (US) LLP

(57) ABSTRACT

A self-auscultation device and method of using the self-auscultation device to listen to a target anatomy is described. The self-auscultation device includes a chest piece to receive a listening device, such as an earphone. The listening device is mounted in the chest piece to detect a sound from the target anatomy, through the chest piece. The listening device can operate in a self-auscultation mode to adapt the listening device to generate audio data corresponding to the detected sound. An equalization filter can be applied to the audio data to compensate for a frequency response of the listening device. A data processing system can compare the audio data to predetermined auscultation data to determine a health condition of the target anatomy. Other embodiments are also described and claimed.

20 Claims, 13 Drawing Sheets

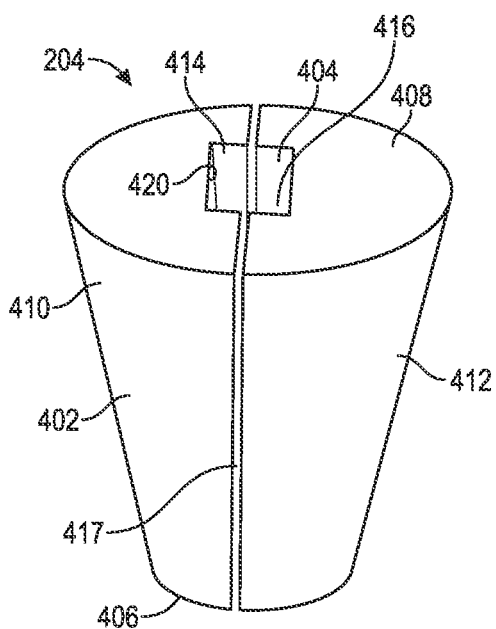 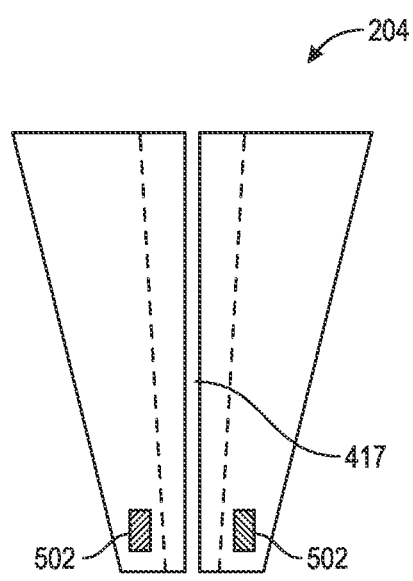
FIG. 4  FIG. 5
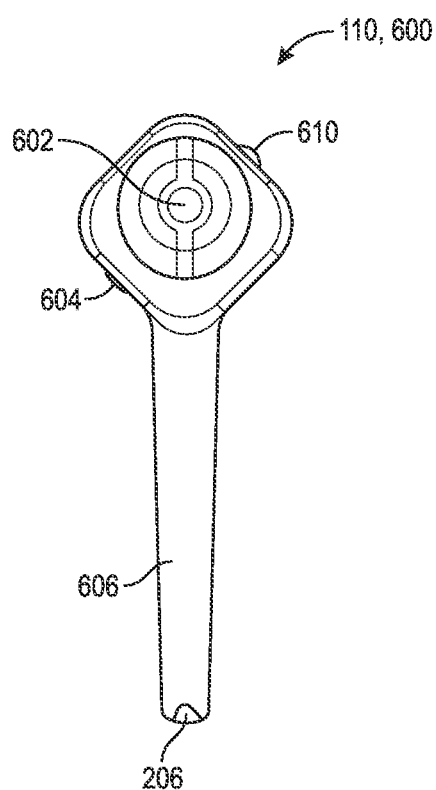
FIG. 6

SELF-AUSCULTATION DEVICE AND METHOD

This application is a continuation of co-pending U.S. patent application Ser. No. 17/313,966, filed on May 6, 2021, which claims the benefit of priority of U.S. Provisional Patent Application No. 63/021,581, filed on May 7, 2020, and these applications are incorporated herein by reference in their entirety to provide continuity of disclosure.

BACKGROUND

Field

The present disclosure relates to devices used to monitor a target anatomy. More specifically, the present disclosure relates to devices used to listen to body organs.

Background Information

Medical listening devices, such as stethoscopes, have been used to listen to sounds created within the human body. Two of the main applications for medical listening devices include monitoring the sounds of the heart and the lungs. Medical practitioners are able to use auscultation to assess the characteristics of the sounds received from a stethoscope device to determine a level of disease that may be affecting the heart or lungs.

Of particular relevance and concern in today's society is the spread of contagious viral pathogens that can become responsible for a very large number of viral infections that can overwhelm our healthcare infrastructure. Of particular concern are viral infections that negatively affect the health of the patient's lungs because over time those type of infections can require the patient to be placed on a mechanical ventilator in the intensive care unit of a hospital. One of the most effective methods of slowing the rate of increase in the spread of respiratory viral infections is to isolate infected patients experiencing mild or moderate symptoms by having them 'self-isolate' at their place of residence.

A noteworthy aspect within the scope of sending patients home to self-isolate is that health care providers never send patients home with a stethoscope to self-monitor the health condition of their lungs for two significant reasons. First, patients do not typically have medical training enabling them to interpret the auscultation sounds made by human lungs that are in the state of ill health. Second, and perhaps more importantly, the very natural fundamental act of "inhaling a breath" or "exhaling a breath" while a patient is attempting to monitor their own lung health with a stethoscope radically disturbs the ability of a patient to actually distinguish and interpret the sounds coming from their lungs. More specifically, the sounds of the air rushing through the patient's mouth cavity during inhalation or exhalation imparts significant 'rushing air sounds' into the patient's Eustachian tubes leading to their inner ear canal, and thus, contributes white noise acoustic energy that disrupts their ability to clearly discern the actual 'lung health sounds' arriving at their eardrum through the stethoscope. In summary, it is not possible for a patient to accurately self-monitor the health sounds and health status of their own lungs using a stethoscope.

As an alternative, some patients infected with a contagious respiratory virus and ordered to self-isolate at home and self-monitor their symptoms have been provided with a pulse oximeter electronic device enabling them to "indirectly" monitor the health of their lungs by tracking their blood oxygen SpO2 saturation levels at home. Their doctor will request for the patient to monitor their blood oxygen SpO2 saturation level daily and if it drops below a set lower limit, e.g., 93 or 94, then the patient is instructed to contact their health care provider. The main problem with relying on a pulse oximeter electronic device for monitoring the health of the lungs is that the blood oxygen SpO2 saturation measurement is only an "indirect" indicator of the health status of a patient's lungs. The key problem with 'indirectly' monitoring SpO2 to gain insight into a condition of deteriorating lung health is that as soon as the human body starts to experience a slightly lower SpO2 level, e.g., 96 or 97 m the patient's autonomic nervous system stimulates the patient's diaphragm muscle to very slightly increase the patient's breath per minute rate (BPM) by 2 or 3 breaths to compensate and keep the patient's SpO2 level at an acceptable reading of 98 or 99. Over time as the patient's lung health continues to deteriorate and the capacity of their lungs to exchange $CO_2$ and $O_2$ continues to degrade their autonomic nervous system once again in concert with the diaphragm muscle slightly increases the patient's breath per minute rate by another 2 or 3 breaths per minute. This ongoing mechanism of incremental progressive increases in the patient's respiratory rate (breaths per minute) occurs without any conscious awareness on the part of the patient and results in blood oxygen SpO2 saturation readings that appear normal but do not accurately reflect the deteriorating health of the patient's lungs. In summary, the pulse oximeter electronic device is only capable of providing an "indirect" measure of a patient's lung health because the human body is inherently capable of naturally adapting to a lower SpO2 level by simply increasing the number of breaths per minute performed by the diaphragm muscle, thus compensating for lower SpO2 levels and restoring SpO2 to normal levels, e.g., 98 or 99.

It is understood that the worst case scenario resulting as a consequence of relying on a pulse oximeter to "indirectly monitor" lung health by measuring SpO2 saturation has been that after 5-7 days of slowly increasing the patient's respiratory rate the patient's diaphragm muscle starts to become exhausted and then the patient's respiratory rate begins to slow and, as a result, their SpO2 saturation readings drop rapidly to 'insufficient' levels, e.g., 92 or 93. Upon calling their health care provider, the patient is very likely to receive instructions to go immediately to the nearest emergency room. At this point the patient is probably in urgent need of supplemental oxygen. Upon arrival at the hospital, if the patient's diaphragm muscle is exhausted beyond recovery and supplemental oxygen does not raise their SpO2 levels, they will be moved directly into the Intensive Care Unit to be placed on a mechanical ventilator to assist their diaphragm muscle by mechanically forcing supplemental oxygen into their ailing lungs.

SUMMARY

Existing stethoscopes can be used by a medical practitioner to listen to a target anatomy of a patient, but not when the patient is in self-isolation, remote from the medical practitioner. Accordingly, self-isolating patients could benefit from access to a cost-effective device that would support their efforts to self-monitor any symptoms of deteriorating health in their lungs. This ability for self-isolated patients to directly monitor the sounds from their lungs (or other organ) and to share those sounds with their doctor would ensure the patient does not develop a severe case of pneumonia (or other health condition).

For patients with viral infections affecting their respiratory tract, the primary cause of death is lack of oxygen due to fluid in the lungs. Having the ability to remotely share lung sounds with their healthcare provider would likely reduce the chance that a patient's condition deteriorates into a serious case of Acute Respiratory Distress Syndrome or pneumonia requiring them to be transported directly to the Intensive Care Unit (ICU) immediately. With healthcare providers monitoring a remote patient's lung sounds daily they should be able to hear the degradation of the patient's lung health over time and make the decision to bring them to the hospital before they have deteriorated into a serious case of pneumonia requiring urgent admission to the ICU. For infected patients that maintain mild symptoms during self-isolation, the daily monitoring of the health status of their lungs would help reduce their levels of stress and thus reduce the potential for them to insist on an in-person appointment at a doctor's office or hospital ER. Reducing the number of in-person appointments helps by reducing the potential for the infected patient to possibly spread the virus to doctors, nurses, first responders, or others that they may encounter on their trip to the doctor's office or hospital ER.

In contrast to the unfeasible use of a traditional stethoscope for self-isolating patients to perform self-auscultation, the description below provides an effective solution that supports the ability of a self-isolating patient to monitor the health status of their lungs while also participating in remote health consultations with their medical provider. Additionally, in contrast to self-isolating patients using a pulse oximeter to 'indirectly' monitor lung health through recording blood oxygen SpO2 saturation the present invention provides patients with a much more accurate 'direct' measure of lung health by recording their lung health sounds while also participating in remote health consultations with their medical provider.

A self-auscultation device and method is described below, which addresses the shortcomings of existing medical listening devices. The self-auscultation device allows self-isolated patients to directly monitor sounds from their lungs (or other organ) and to share those sounds with their healthcare provider. In an embodiment, the self-auscultation device includes a chest piece having a concavity that faces a first direction, and a chest piece channel extending through the chest piece in a second direction from the concavity. The concavity receives sounds from a chest wall of a patient and directs the sounds through the chest piece channel. The chest piece channel is configured to receive a listening device, either directly or indirectly, for self-auscultation of a target anatomy. For example, the chest piece channel can be sized to directly fit the outer surface of the listening device. Alternatively, the self-auscultation device can include an adaptor to receive the listening device indirectly. More particularly, the listening device can be received by the adaptor, and the chest piece channel can fit an outer surface of the adaptor. Accordingly, an adaptor channel can place the concavity in fluid communication with the listening device when the adaptor is mounted within the chest piece channel.

In an embodiment, the self-auscultation device is a dual-bell-type self-auscultation device having a second concavity facing the second direction. The adaptor can rotate between a first configuration in which the space is in fluid communication with the concavity and a second configuration in which the space is in fluid communication with the second concavity. An adaptor recess can be directed toward one of the concavities in each of the configurations. In an embodiment, the concavities are differently sized to accommodate different frequencies of sounds, e.g., generated by different target anatomies. The sounds can be conducted from the concavities to the listening device held by the adaptor.

The listening device, which may be mounted in the adaptor, can be an off-the-shelf, readily-available earphone. The listening device includes a microphone configured to detect a sound from the concavity, and one or more processors to generate audio data corresponding to the sound. The listening device also includes a transmitter, e.g., a low power Bluetooth radio, configured to wirelessly transmit the audio data to another device, such as to a smartphone or tablet computer of the patient. The smartphone or tablet of the patient may transmit audio data to a data processing system of a healthcare provider. The connected devices can form a self-auscultation system, or a remote health monitoring system, capable of performing a self-auscultation method.

In an embodiment, the self-auscultation method includes adapting the listening device or the mobile device of the patient to accurately record self-auscultation sounds. The method can include determining whether a device (e.g., the listening device or the mobile device of the patient) is being used for self-auscultation of a target anatomy. In response to determining that the device is being used for self-auscultation, the device can be set to operate in a self-auscultation mode. For example, one or more of a microphone configuration, a voice activation configuration, a noise cancellation configuration, a voice assistant configuration, a battery usage configuration, a proximity sensor configuration, a Bluetooth transmission protocol configuration, or a device pairing configuration can be set for the listening device or the mobile device. The listening device may then detect a sound from the target anatomy and, based on the self-auscultation mode setting, accurately generate audio data corresponding to the sound. In an embodiment, a data processing system, such as the mobile device of the patient or a computer or server of the healthcare provider, can determine, based on a comparison between the audio data generated by the listening device and predetermined auscultation audio data, whether the sound matches a predetermined auscultation sound. Based on the comparison, the data processing system can determine whether the sound from the target anatomy indicates a health condition. For example, when the sound matches a pre-recorded sound of another patient experiencing symptoms of a viral lung health condition, the data processing system can determine that the patient is also likely to have the viral lung health condition.

In an embodiment, a self-auscultation method includes validating the listening device for use in performing the self-auscultation method. The method includes generating, by a sensor of the listening device, one or more test signals corresponding to one or more test tones, emitted by the mobile device. The test tones can include sounds emitted by a speaker of the mobile device. The method includes determining, based on a comparison between the one or more test signals and the one or more test tones, an equalization filter to compensate for a non-linear frequency response of the listening device. The comparison can be between frequency content of the test signals and predetermined frequency content of the one or more test tones. The equalization filter, when applied to audio data corresponding to sounds detected by the earphone, produces a linear frequency response for the earphone. The validated listening device can generate audio data corresponding to sounds from self-auscultation of a target anatomy. The equalization filter may be applied to the audio data to produce accurate self-auscultation audio data for comparison to predetermined auscultation sounds, which may indicate whether the patient has a health condition.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 is perspective view of an adaptor of a self-auscultation device, in accordance with an embodiment.

FIG. 5 is a sectional view of an adaptor of a self-auscultation device, in accordance with an embodiment.

FIG. 6 is a front view of a listening device, in accordance with an embodiment.

DETAILED DESCRIPTION

Figure 1:
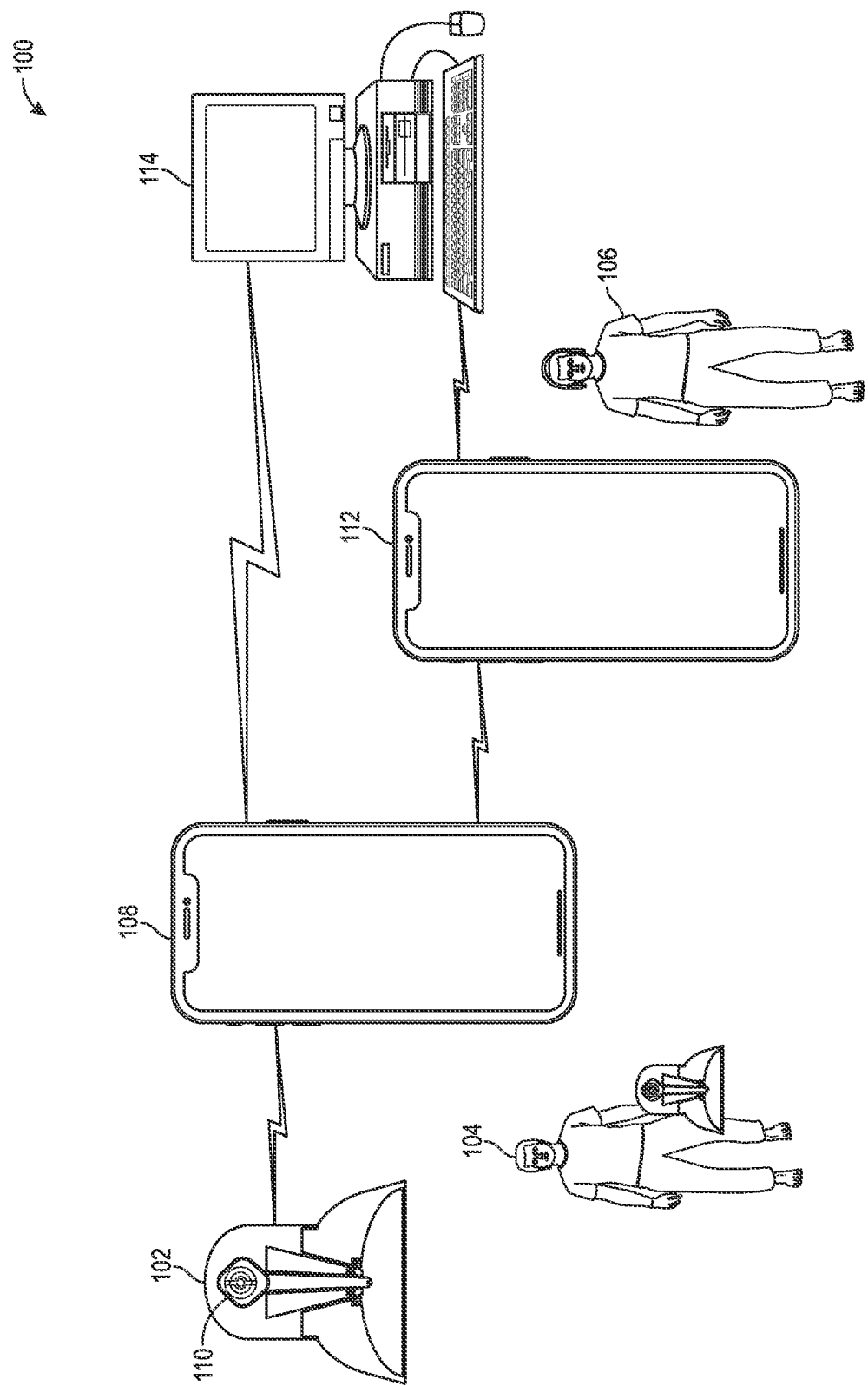
FIG. 1 is a system level block diagram of a remote health monitoring system, in accordance with an embodiment.

Embodiments describe a self-auscultation device and method. The self-auscultation device can be used to evaluate a health condition of an organ, such as the lungs. The self-auscultation device may, however be used in other applications, such as to evaluate a health condition of the heart. Accordingly, description of the self-auscultation device being used in a particular application below is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a self-auscultation device. Similarly, "proximal" may indicate a second direction opposite to the first direction. Such terms are provided to establish relative frames of reference, however, and are not intended to limit the use or orientation of a self-auscultation device to a specific configuration described in the various embodiments below.

In an aspect, a self-auscultation device is provided that includes a chest piece and/or adaptor to direct sounds from a target anatomy through a channel or space. A listening device, such as an off-the-shelf earphone, can be mounted on or in the chest piece and/or adaptor such that the sounds are received by a microphone of the listening device. Accordingly, a low-cost and portable self-auscultation device can be provided that uses readily available electronics to generate, and optionally process, audio data corresponding to sounds from the target anatomy.

In an aspect, a method of performing self-auscultation using a self-auscultation device includes adapting a listening device (such as an earphone), or another device wirelessly paired to the listening device (such as a smartphone or tablet), to operate in a self-auscultation mode. The self-auscultation mode can adapt the device(s) to operate in an application-specific mode that configures hardware and/or software of the device(s) to more accurately perform self-auscultation.

In an aspect, a method of performing self-auscultation using a self-auscultation device includes validating a listening device for use in self-auscultation. A listening device wirelessly paired to another device can receive input test signals corresponding to test tones emitted by the other device. Based on the input test signals, a frequency response of the listening device can be evaluated. For example, a linearity of the frequency response may be assessed. An equalization filter can be determined, and can be applied to audio data generated by the listening device to achieve a more linear frequency response. Accordingly, the frequency response of the listening device can be compensated for. Validation of the listening device allows accurate and consistent audio data to be generated across a range of listening devices that may be used for self-auscultation.

Having discussed various aspects above, a general overview of the detailed description is now provided before providing additional details with respect to the figures. A self-auscultation device and method is provided for patients who may have contracted a respiratory virus to allow their doctor to remotely monitor the health of their lungs during their recovery in self-isolation. More specifically, a hand held Bluetooth enabled chest piece is provided in combination with a mobile software application that guides the patient thru the lung monitoring procedure, records their lung sounds, and then transmits the lung sound recordings to their doctor. Healthcare providers can benefit by receiving daily lung sound recordings without having to send a nurse or medical technician into close contact with a patient infected with a contagious respiratory virus.

Healthcare providers treating remote self-isolating patients infected with a respiratory virus can be in the difficult position of trying to understand the patient's lung health status based on 'indirect' lung health data that they infer from the general symptomatic updates provided by a patient. The present invention enables healthcare providers the ability to make healthcare decisions for the remote patient based on 'direct' lung health data, e.g., lung sound recordings. Access to 'direct' lung health data on a daily basis can provide doctors greater confidence in the efficacy of their decision when instructing a patient to continue their self-isolation and self-monitoring of symptoms.

The self-auscultation device and method adapts low-cost readily available wireless, e.g., Bluetooth, earpieces to enable their use for remote medical monitoring. The self-auscultation device and method allows patients and healthcare workers to collaboratively monitor the lung health of remote patients when the patient has been instructed to 'self-isolate' due to being infected with a contagious respiratory virus. The self-auscultation device and method allows self-isolated patients with a viral respiratory infection to remotely collaborate with healthcare providers to monitor their lung health by recording and then sharing the symptomatic sounds from their lungs. The procedure proposed for patients to monitor and record the sounds from their own lungs will be referred to as "self-auscultation."

The self-auscultation device can include a small, fist-sized, drum-like, device that a patient can hold against their chest to allow for monitoring and recording of the sounds from their lungs. The device includes a mechanical structural component that will be referred to as the chest piece. The bottom side of the chest piece is designed to be covered with a thin diaphragm disc that, when placed in contact with the patient's chest, helps to collect and conduct sound waves emanating from the heart and lungs. On the opposing 'upper side' of the chest piece the design of the self-auscultation device can include a conical tapered recess that is referred to as the chest piece channel. The chest piece channel can receive an adaptor and/or a listening device, e.g., a wireless earpiece. The adaptor can be compatible with the audio functionality and specific mechanical dimensions of one or more models of wireless earpieces. After installing the adaptor, in combination with the compatible wireless earpiece, the chest piece can then be fitted with an isolation dome (or cap) component covering and protecting the wireless earpiece from incidental contact while the device is being used. As such, the sequence of assembling the self-auscultation device for use can include: separating portions, e.g., halves, of the adaptor; re-assembling the portions onto a portion, e.g., a stem or microphone boom, of a wireless earpiece; seating the combined adaptor and wireless earpiece into the chest piece channel; turning on the wireless earpiece; and attach the isolation dome onto the upper rim of the chest piece. The assembled self-auscultation device can then be ready to be used by the patient to monitor and record sounds from their heart or lungs.

The patient can install and run a self-auscultation mobile application, referred to herein as a "health sound recorder application," on their smartphone or tablet. The health sound recorder application can include instructions stored on a non-transitory machine readable medium which, when executed by one or more processors of the smartphone or tablet, causes the smartphone or tablet to perform the self-auscultation method described below.

The self-auscultation software application allows the patient to configure an account on a remote database administered by their healthcare provider. The patient can perform a setup process by entering their personal information. The patient can use the operating system of their computing device, e.g., their smartphone or tablet, to pair their computing device with the wireless earpiece installed in the chest piece. After pairing, the self-auscultation software application can perform a test to confirm that it can communicate with the wireless earpiece.

When the software setup is complete and the wireless communication link is verified, the self-auscultation software prompts the user to select from one of several test modes that can include "record lung sounds" or "record heart sounds." The test mode(s) can include display, on the computing device, a 2D or 3D graphic image of a human chest with an "x" marking each of the contact points where the patient will place the diaphragm surface of the self-auscultation device to allow the software to monitor and record the sounds. The self-auscultation software can communicate additional procedural instructions via text displayed on the computer display and/or via audio content from the computer's speakers. The procedural instructions for the selected test mode may include instructions for the patient's body position: to stand, sit, or lie down prior to continuing with the test. Alternatively, the procedural instructions for a "monitor lungs" test mode may include requests for the patient to manually control their breathing pattern such as: breathe in, or breathe out, or instructions for when to hold their breath. The procedural instructions may also include instructions for other breathing patterns such as: shallow breath, normal breath, or deep breath.

After completing the sound recordings for the selected test mode, the patient can instruct the self-auscultation software application to transmit their self-auscultation sound recordings to their healthcare provider for review. If needed the self-auscultation software can also support the functionality needed for the patient's healthcare provider to remotely interact with the patient via a two-way video call as the patient is collecting the self-auscultation sound recordings for the selected test mode.

In the event of a highly contagious viral pandemic that spreads easily via respiratory droplets, the primary treatment method used by healthcare providers for infected patients with mild symptoms is to instruct them to self-isolate and self-monitor their symptoms. This decision to instruct patients to self-isolate and self-monitor symptoms is most often justified based on the following reasons: in a viral pandemic the health care facilities/system can become overloaded and all available medical personnel are attending to patients with more serious/advanced symptoms; and if the patient has been exposed to a highly contagious viral pathogen and their symptoms are mild, self-isolating and self-monitoring can avoid the need for a non-urgent office visit that could unnecessarily expose others to the highly contagious virus. The healthcare provider can remotely monitor the patient's health through self-monitoring by the patient, in case they develop worsening symptoms. The healthcare provider can periodically re-evaluate the patient's symptoms to determine if their health has deteriorated to a state requiring medical attention at a hospital or urgent care facility.

Self-monitoring is typically performed using existing tools, such as stethoscopes. These existing solutions, however, have drawbacks. The self-auscultation device and method provides advantages that resolve or mitigate the disadvantages of the current solutions. Those disadvantages include the failure to solve the following four problems.

First, self-isolation when ill is stressful and worsens a patient's mental health. When suffering from a viral infection in isolation it can be difficult for patients to make well-reasoned self-care decisions such as what to eat or how much to eat because their emotional responses can become elevated. When a person with a respiratory viral infection is relegated to self-isolation for days and weeks on end, their stress builds and can give rise to emotional distress symptoms such as anxiety, depression, and a reoccurring fear associated with constantly second guessing the meaning of any change in their symptoms and wondering if their medical condition is possibly becoming worse. Whereas existing listening medical devices do not solve this problem, the self-auscultation device described below helps. As a result of the patient using the self-auscultation device and health sound recorder application to record and transmit their lung sound recordings for review by their healthcare provider, the patient may feel safer. The patient's interaction with the doctor on a daily basis makes them feel cared for knowing their doctor is actively monitoring their lung sounds daily for any potential degradation in the health of their lungs.

Second, self-monitoring lung symptoms with a stethoscope is problematic. The challenges confronting an isolated patient who is trying to self-monitor their own lung symptoms using a stethoscope can be substantial. When a patient uses a stethoscope to listen to their own lung sounds it turns out that the sounds from the patient's own breathing interferes with the ability of the patient to clearly hear the sounds from their lungs. The patient needs to try and actively ignore the sounds from each deep breath as it reaches their ears through their Eustachian tube while simultaneously trying to focus just on the sounds of their lungs being conducted by the stethoscope. An additional challenge arises in that typical patients lack the medical training required to be able to identify the characteristic sounds associated with the different symptomatic sounds associated with typical lung abnormalities. The self-auscultation device is easy for an isolated patient to use to monitor their lung sounds. The self-auscultation device does not require the use of a stethoscope, and thus, it avoids the inherent audio interference from the sounds of their own breathing. The self-auscultation device enables the patient and healthcare worker to listen to the patient's recorded lung sounds to assess their lung health and determine if the patient should continue to self-isolate and self-monitor. The self-auscultation device also educates patients about symptomatic lung sounds. The health sound recorder application can contain a pre-recorded library of lung sounds including examples of both normal and abnormal lung sounds, thus allowing a patient to compare their own lung sounds to the lung sounds provided in the library. Additionally, in the event of a pandemic due to a virus that attacks the respiratory system, the health sound recorder application can receive periodic library sound updates with the most current abnormal symptomatic lung sounds being observed by the doctors on the front lines of the pandemic.

Third, remote monitoring of lung health is difficult for healthcare providers. The primary method of assessing lung health relies on a doctor placing the chest piece of a stethoscope against the patient's chest while listening to the sounds of deep breaths. Performing this traditional method of lung assessment on a self-isolated patient with a viral infection requires a trained healthcare professional to travel to the patient's residence of isolation to perform the examination. In the event of a viral pandemic this would increases the healthcare worker's chance of contracting the virus. The self-auscultation device can keep healthcare workers safe. The use of the chest piece and the health sound recorder application capable of recording lung sounds provides a safe and effective alternative to a doctor or nurse traveling to the patient's residence. The daily lung sound recordings automatically sent to the patient's healthcare provider allow doctors and nurses to avoid exposure to a contagious respiratory virus while supporting their ability to monitor and assess the lung health of remote patients who have been instructed to self-isolate.

Fourth, remote health monitoring equipment can be complex and expensive. Health monitoring equipment is complex. Learning to operate remote health monitoring equipment typically requires formal training as a technician, therapist, nurse, or doctor. Most typical patients will not have had any formal training on health monitoring equipment. Additionally, based on the complexity of monitoring human biological systems, such as the lungs, medical equipment intended for remotely monitoring the patient's lung health can be very expensive. In a viral pandemic healthcare providers are unlikely to provide remote health monitoring equipment for all of the patients who have mild symptoms and have been instructed to self-isolate. Of consideration is also the expense of current wireless stethoscope devices and the fact that they cannot be sterilized after use with a patient that has a contagious respiratory virus. As a result doctors and nurses must cover the wireless stethoscope with plastic bags in that case. The self-auscultation device provides an intuitive cost effective medical device for remotely monitoring patients. The self-auscultation device provides a mobile application that can be run on a smartphone or a tablet computer. In today's society a very large percentage of the population has a working knowledge of how to install and operate mobile applications on a smartphone or tablet computer. With recent advancements in the development of user interfaces the mobile app of the present invention will be able to provide to the patient a much simpler and more intuitive user interface than found on most medical instruments. Furthermore, the present invention is not expensive. The wireless earpieces used in the present invention, by comparison to typical medical health monitoring equipment, are cheaper. Additionally, wireless earpieces are readily available. Hundreds of millions of wireless earpieces have been sold over the last decade. Those earpieces already sold, along with the millions of wireless earpieces currently available in the marketplace, can ensure a high availability of wireless earpieces for patients and healthcare providers to be able to fully utilize the self-auscultation device and method described below, for remotely monitoring lung health in the event of a serious viral pandemic.

It is also noted that the self-auscultation device allows the electronics to be removed prior to sterilization and the remaining structural components of the device to be placed in an autoclave or sterilized by other means including liquid emersion. Accordingly, the self-auscultation device can be reused safely.

In view of the above general description, the self-auscultation device and method will now be understood to be advantageous over existing solutions. The following description provides additional details of the self-auscultation device and method.

Referring to FIG. 1, a system level block diagram of a remote health monitoring system is shown in accordance with an embodiment. A remote health monitoring system 100 can include a self-auscultation device 102 used by a patient 104 remotely located relative to a healthcare provider 106, e.g., a doctor. The patient 104 can, in addition to the self-auscultation device 102, have a mobile device 108, e.g., a smartphone or a tablet. The mobile device 108 can be wirelessly paired to a listening device 110 mounted in the self-auscultation device 102 to form a self-auscultation system that can communicate wirelessly with remote data processing systems. More particularly, the mobile device 108 can communicate through communication channels with a healthcare provider device 112 or a remote server 114, one or more of which may be operated by the healthcare provider. The healthcare provider device 112 can be a smartphone of the healthcare provider 106 who is remotely monitoring the patient 104. The remote server 114 can be a data processing system connected to the internet. The mobile device 108, healthcare provider device 112, and/or remote server 114 can have a health sound recorder application installed and running to perform a method of self-auscultation, as described below.

Figure 2:
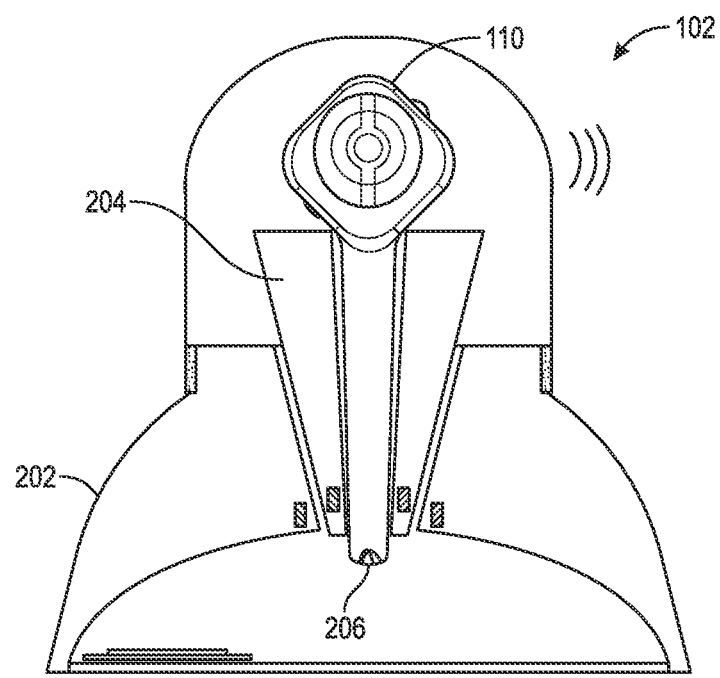
FIG. 2 is a sectional view of a self-auscultation device, in accordance with an embodiment.

Referring to FIG. 2, a sectional view of a self-auscultation device is shown in accordance with an embodiment. The self-auscultation device 102 can be a single-bell-type self-auscultation device 102. More particularly, the self-auscultation device 102 can include a chest piece 202 having a single concavity to receive and conduct sounds from the chest of the patient 104. Furthermore, the chest piece 202 can be configured to receive the listening device 110. For example, the self-auscultation device 102 can include an adaptor 204 that is configured to receive the listening device 110. The adaptor 204 can be mounted in the chest piece 202 while holding the listening device 110, and thus, the sounds conducted through the concavity 302 can arrive at a microphone 206 of the listening device 110. The microphone 206 can detect the sounds for self-auscultation of the patient 104, as described below.

Figure 3:
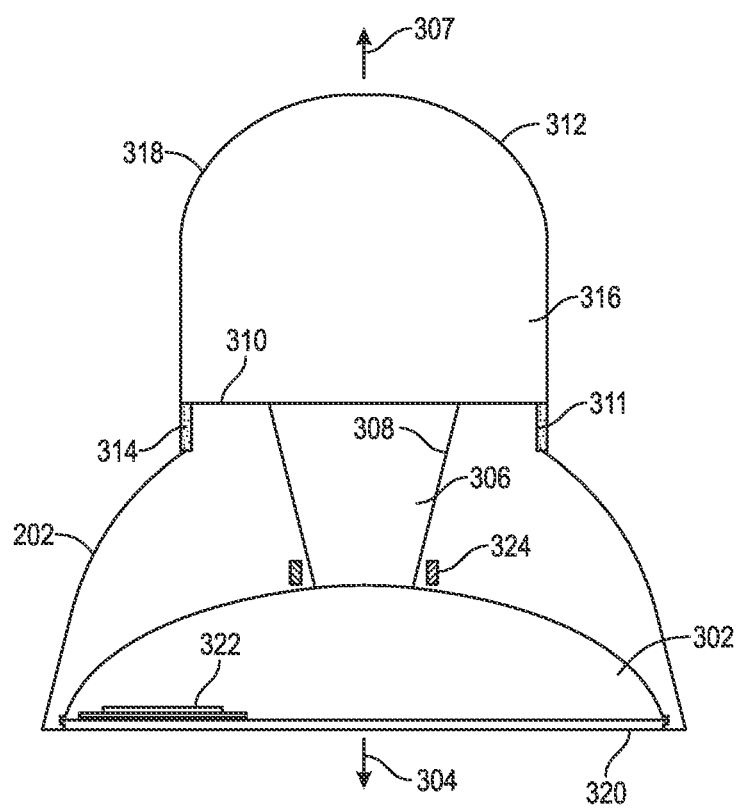
FIG. 3 is a sectional view of a chest piece and cap of a self-auscultation device, in accordance with an embodiment.

Referring to FIG. 3, a sectional view of a chest piece and cap of a self-auscultation device is shown in accordance with an embodiment. The chest piece 202 of the self-auscultation device 102 can include a body having a concavity 302 facing a first direction 304, e.g., a distal direction, such that the concavity 302 receives the sounds proximally from the chest when the chest piece 202 is positioned for self-auscultation.

The chest piece 202 can include a chest piece channel 306 extending through the chest piece 202. For example, the chest piece channel 306 can extend in a second direction 307, e.g., a proximal direction, from the concavity 302 along a central axis of the concavity 302. The chest piece channel 306 can be surrounded by a chest piece channel surface 308 (which can be a portion of an inner surface defining a central lumen of the chest piece body) that is sized and shaped to receive the listening device 110 and/or the adaptor 204. For example, the chest piece channel surface 308 can have a tapered, e.g., a frustoconical, surface to mate with a corresponding surface of the adaptor 204. More particularly, the tapered channel can provide a port to matingly contact the listening device 110 or the adaptor 204 to secure the component within the chest piece 202. Accordingly, the chest piece 202 can include one or more cavities or channels to receive the listening device 110 for self-auscultation of a target anatomy.

In an embodiment, the chest piece 202 includes a mounting wall 310, e.g., a circular mounting wall. The mounting wall 310 can be a proximal face of an exterior surface of the chest piece body and can face the second direction 307, opposite to the direction faced by the concavity 302. Accordingly, the chest piece channel 306 can extend through the chest piece 202 body from the concavity 302 to the mounting wall 310.

The chest piece 202 can include a lip or rim 311 extending around the mounting wall 310 to receive a cap 312. The cap 312 may be mountable on the chest piece 202. For example, the rim 311 can include a securement feature 314 to receive and retain the cap 312. The securement feature 314 may be a threaded connection between the rim 311 and the cap 312. More particularly, the rim 311 may be threaded to allow mating threads of the cap 312 to be screwed onto the chest piece 202. Alternatively, the securement feature 314 can include hinging features, similar to the hinge illustrated in FIG. 19, to secure the cap 312 to the chest piece 202. Alternatively, the chest piece 202 can include a securement feature 314, such as an O-ring or magnets, extending around the rim 311. The securement feature 314 can provide a retention force, e.g., via a press fit or magnetic attraction, to retain the cap 312 when the cap is mounted on the chest piece 202.

When the cap 312 is mounted on the chest piece 202, the cap encloses an isolation cavity 316. The isolation cavity 316 can be defined between a cap wall 318 and the chest piece 202. For example, the isolation cavity 316 can be a space between the mounting wall 310 of the chest piece 202 and an interior surface of the cap wall 318. Accordingly, the chest piece channel 306 can place the concavity 302 in fluid communication with the space.

The cap 312 can reduce the likelihood of environmental noise interfering with the quality and accuracy of self-auscultation audio data. The cap 312 can also protect the listening device 110 from being bumped, touched, or dislodged while moving the chest piece 202 assembly from point to point while recording self-auscultation data. The cap 312 can function as an air tight dome. For example, the securement feature 314 can be an O-ring that provides a hermetic seal between the cap 312 and the chest piece body. Advantageously, the cap 312 can also be sized and shaped to provide a convenient handle for gripping and manipulating the self-auscultation device 102 during use.

In an embodiment, the self-auscultation device 102 includes a diaphragm 320 covering a distal port of the concavity 302. Accordingly, the concavity 302 can be defined between the diaphragm 320 and an interior wall of the chest piece 202. The diaphragm 320 can be disc-shaped, and may be formed from a piece of plastic or fiberglass, e.g., fabricated from plastic or fiberglass stock using die cutting. Additionally, the diaphragm disc can be fabricated from plastic by thermoplastic molding or injection molding processes.

The diaphragm 320 may be attached to a lower edge of the auscultation bell using a tension or compression attachment method that creates a hermetic seal. The air tight seal contributes to ensuring maximal sound wave energy is transmitted to the microphone 206 of the listening device 110. When the diaphragm disc is mounted in the auscultation chest piece 202 and held against a chest wall of the patient 104, the diaphragm 320 vibrates due to the mechanical vibration of the body organs. The diaphragm 320 begins to vibrate much like the surface of an eardrum and in turn vibrates the air in the auscultation bell of the chest piece 202, creating sound waves.

In an embodiment, the self-auscultation device 102 includes a digital identification tag 322. The digital identification tag 322 can be mounted on the chest piece 202. For example, the digital identification tag 322 can be mounted on an inner surface of the diaphragm 320. In an embodiment, the digital identification tag 322 is attached to the diaphragm 320, or another location on the chest piece 202 or cap 312, by an adhesive bond.

The digital identification tag 322 can be, for example, a near-field communication tag or a Bluetooth beacon tag. Accordingly, the digital identification tag 322 can be fabricated on a reel-to-reel type of conductive ink printing process. The digital identification tag 322 can store data, such as an encrypted identifier, e.g., an encrypted serial number, uniquely identifying the self-auscultation device 102. Accordingly the digital identification tag 322 can be used during a setup procedure to create a software pairing between the self-auscultation device 102 and the health sound recorder application. To effect the software-based pairing between the device and the mobile application, the software can record in memory the encrypted identifier of the self-auscultation assembly. Also, the data content in the digital identification tag 322 can include a URL link to assist during initial setup by helping the user to conveniently locate, download, and install the health sound recorder application. Additionally, the digital identification tag 322 can hold encrypted codes that can be used to prevent counterfeit hardware products from being used with the genuine health sound recorder application.

In an embodiment, the chest piece 202 includes one or more chest piece magnets 324. The chest piece magnet(s) 324 can be positioned adjacent to the chest piece channel 306. For example, the chest piece magnet 324 can be embedded within the chest piece channel surface 308, e.g., during an injection molding process. Alternatively, the chest piece magnet 324 can be glued into a matching recess formed in the chest piece 202. As described below, the chest piece magnet 324 can be located such that, when the adaptor 204 is mounted within the chest piece channel 306, the chest piece magnet 324 interacts with a corresponding magnet of the adaptor 204. The chest piece magnet 324 can be fabricated from rare-earth neodymium alloy (NdFeB), and thus, can provide a strong retention force to secure the adaptor 204 to the chest piece 202. More specifically, retention magnets contribute forces to assist in the retention of the adaptor 204 when it is installed in the adaptor port provided by the chest piece channel 306.

Referring to FIG. 4, a perspective view of an adaptor of a self-auscultation device is shown in accordance with an embodiment. The adaptor 204 can have an adaptor wall 402 sized to fit into the chest piece channel 306. For example, the adaptor wall 402 can have an outer surface that is the same size and shape as the inner surface of the chest piece channel 306. Accordingly, the adaptor 204 can be loaded into the chest piece channel 306 to form a press fit between the adaptor wall 402 and the chest piece channel surface 308.

The adaptor 204 includes an adaptor channel 404 extending through the adaptor 204. More particularly, the adaptor channel 404 can extend from a distal adaptor end 406 to a proximal adaptor end 408. Accordingly, when the adaptor 204 is mounted within the chest piece channel 306, the adaptor channel 404 can place the concavity 302 in fluid communication with a space proximal to the adaptor 204. The space may be a surrounding environment, e.g., when the cap 312 is not mounted on the chest piece 202. Similarly, the space can be the isolation cavity 316 when the adaptor 204 is mounted within the chest piece channel 306 and the cap 312 is mounted on the chest piece 202.

The adaptor 204 can be fabricated in one or more pieces. For example, the illustrated embodiments is a two piece adaptor 204. In such case, the adaptor 204 can include a first adaptor portion 410 and a second adaptor portion 412. The portions can be mirror images of each other, and may be assembled to each other to combine into the adaptor whole. The first adaptor portion 410 can include a first portion channel 414, and the second adaptor portion 412 can include a second portion channel 416, which may be combined to form the adaptor channel 404. More particularly, the first portion channel 414 can be defined by a recess in the surface of the first portion 410 that faces a recess in the surface of the second portion 412 defining the second portion channel 416, and when the portions are assembled with the recesses facing each other, the recesses can form the adaptor channel 404.

In the case of the multi-portion adaptor 204, the portions can be joined along a seam 417. It will be appreciated, however, that in the case of a monolithic adaptor 204 (e.g., having a single portion fabricated by an injection molding process) there may be no seam 417 and the entire structure of the combined portions of FIG. 4 can be provided in a single body.

The adaptor channel 404 can be sized and shaped to receive the listening device 110. For example, the listening device 110 may include a microphone boom having a circular or rectangular outer surface profile. The adaptor channel 404 can have a profile 420 that is ellipsoidal (to receive the circular microphone boom) or polygonal (to receive the rectangular microphone boom). Accordingly, the surface defining the adaptor channel 404 can conform to an outer surface of the listening device 110.

Anticipating that the microphone boom of the listening device 110 may contain a wireless antenna structure, the adaptor 204 can be fabricated from one of several different types of plastic materials that do not significantly impede radio waves from wireless, e.g., Bluetooth, radio. More particularly, the adaptor 204 can be fabricated from materials having low, e.g., near zero, dielectric loss factor. Examples include polyphenyl (PPL), polyvinyl chloride (PCV), and acrylonitrile butadiene styrene (ABS).

The adaptor 204 can adapt the mechanical dimensions and audio functionality of the listening device 110, e.g., an off-the-shelf earphone, to become compatible with a standard receiving port in an application-specific chest piece 202. The primary mechanical functional benefit derived from a successful 'adaptation' is the listening device 110 being held securely in the correct position to allow the microphone 206 of the listening device 110 to pick-up the auscultation sound wave emanating from the diaphragm 320. The listening device 110 can then transmit the sounds to the mobile device 108 where they can be recorded by the health sound recorder application.

Referring to FIG. 5, a sectional view of an adaptor of a self-auscultation device is shown in accordance with an embodiment. The adaptor 204, like the chest piece 202, can include a retention magnet. More particularly, the adaptor 204 can include one or more adaptor magnets 502. The adaptor magnets 502 can be positioned such that, when the adaptor 204 is mounted within the chest piece channel 306 (FIG. 2), the adaptor magnet 502 is adjacent to the chest piece magnet 324. More particularly, in the assembled configuration, the chest piece magnet 324 can interact magnetically with the adaptor magnet 502 to retain the adaptor 204 within the chest piece 202. Like the chest piece magnet 324, the adaptor magnet(s) 502 can be encased in the walls of the adaptor portion(s) during an injection molding process, or by subsequently being glued into matching recesses in the walls.

Referring to FIG. 6, a front view of a listening device is shown in accordance with an embodiment. The listening device 110 can be an earphone 600. Wireless earpieces were originally designed to function as a "cable replacement" technology to carry voice communication between the user's ear and the user's cell phone. The self-auscultation device 102 re-purposes these popular, cost-effective, readily-available wireless earpieces to be used in an application-specific chest piece 202 to detect auscultation sounds, and to generate and transmit audio data corresponding to the sounds to the health sound recorder application running on the mobile device 108. The wireless earpiece may support firmware functions including an auscultation mode, as described below, that allows the health sound recorder application to set the wireless earpiece into an application-specific mode that includes specific settings that optimize the wireless earpiece for being used in the self-auscultation device 102 to monitor heart or lung sounds.

The listening device 110 can be a wireless, e.g., Bluetooth, earpiece having a transmitter (not shown) to provide wireless communication between the listening device 110 held in the self-auscultation device 102 and the mobile device 108. The wireless earpiece component can be a small electronic communication device containing the microphone 206, an earphone speaker 602, a battery, one or more processors, e.g., a system-on-a-chip (SoC), a wireless transceiver including the transmitter (for example, a Bluetooth Low Energy—BTLE transceiver), an antenna structure, and user interface elements 604 (e.g., lights, buttons, or switch controls). Companies that manufacture wireless earpieces utilize a wide variety of mechanical structure designs to house their electronic components. It will be appreciated that all models of wireless earphones are contemplated as being within the scope of this description.

In an embodiment, the listening device 110 includes a boom 606 to support the microphone 206. The boom 606 can hold the microphone 206 at the end of a stem, opposite from the earphone speaker 602 and nearer to a user's mouth. The shape and dimensions of the boom 606 holding the microphone 206 varies widely among manufacturers. More particularly, different boom 606 models can have different profiles 420 (round or rectangular) and lengths. The length of the boom 606 can be accounted for by the adaptor 204. More particularly, the adaptor 204 can have a length that allows the microphone to be exposed to detect a sound from the concavity 302 when the listening device 110 is mounted within the adaptor 204 and the chest piece channel 306. The one or more processors of the listening device 110 can generate audio data corresponding to the sound. Furthermore, the transmitter can be configured to wirelessly transmit the audio data. For example, the transmitter can be a low power Bluetooth radio configured to wirelessly communicate the audio data to mobile device 108.

In an embodiment, the listening device 110 includes a proximity sensor 610. The proximity sensor 610 can allow the one or more processors of the listening device 110 to determine when the earpiece has been installed into the users ear or removed from the users ear. Accordingly, the proximity sensor 610 can be monitored by the mobile device 108 to make decisions and provide desired functionality, as described below.

Figure 7:
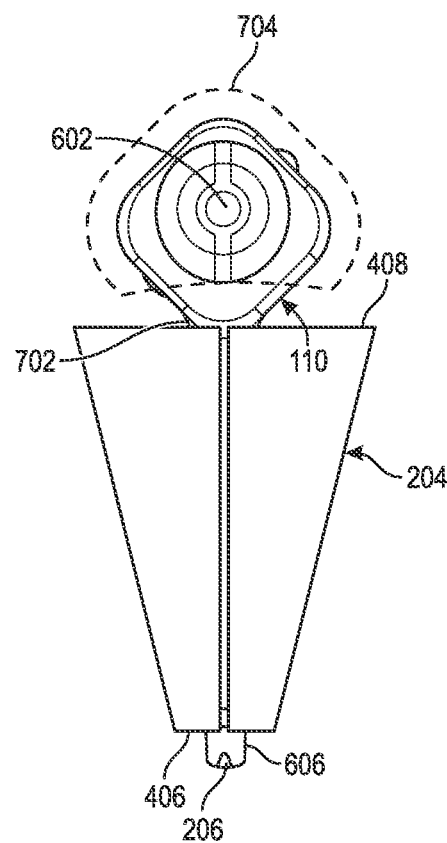
FIG. 7 is a front view of a hooded listening device mounted in an adaptor, in accordance with an embodiment.

Referring to FIG. 7, a front view of a hooded listening device mounted in an adaptor is shown in accordance with an embodiment. The adaptor 204 can include precision interior dimensions accommodating the proprietary length and cross-sectional shape of the microphone boom 606 of the listening device 110. Additionally, the exterior shape and dimensions of the adaptor 204 can conform to the required shape and dimensions of the adaptor port in the chest piece 202.

The adaptor 204 can be assembled around the listening device 110 such that the listening device 110 is clamped between the adaptor portion(s). For example, in the assembled configuration, the microphone boom 606 can extend longitudinally through the adaptor 204. The microphone 206 can be located at one end of the adaptor 204, e.g., distal to the distal adaptor end 406, and the earphone speaker 602 can be located at another end of the adaptor 204, e.g., proximal to the proximal adaptor end 408.

The listening device 110 can be secured within the adaptor 204 in any of several manners. For example, an inner surface of the adaptor 204 defining the adaptor channel 404 can be covered by a thin layer of low-tack pressure sensitive adhesive to assist in the retention of the listening device 110 within the adaptor channel 404. Alternatively, the adaptor 204 can squeeze the listening device 110 when the adaptor 204 plugs the chest piece channel 306, and thus, the listening device 110 can be secured at least in part by friction caused by the compression of the microphone boom 606. Also, the material properties of the adaptor 204 can contribute a coefficient of static friction that contributes to holding the listening device 110 securely. Also, the microphone boom 606 of the earphone 600 may contain ferrous material, and the adaptor magnets 502 can provide additional retention forces to secure the listening device 110 in the adaptor 204.

In an embodiment, an interference fit between a proximal adaptor end 408 of the adaptor 204 and a shoulder contact point 702 of the listening device 110 can support the earpiece and resist movement of the listening device 110 when the self-auscultation device 102 is assembled. Selecting a correct length for the adaptor 204 ensures the tapered earpiece adaptor 204 touches the shoulder contact point 702 of the wireless earpiece, ensuring it remains securely affixed in the intended position and unlikely to slip down and possibly contact the diaphragm 320. The length of the adaptor 204, e.g., between the proximal adaptor end 408 and the distal adaptor end 406, can be sized according to the microphone boom 606 length to provide contact to the shoulder contact point 702 while allowing the microphone 206 to remain exposed below the adaptor 204.

Like the listening device 110 in the adaptor 204, the adaptor 204 may be secured within the chest piece channel 306. The securement may be effected via any of the securement modes described above, e.g., friction or adhesive forces. Alternatively, the adaptor 204 can be secured to the chest piece 202 via magnets, complementary threaded features at the interface of the two components, or other securement features.

In an embodiment, the self-auscultation device 102 includes a hood 704. The hood 704 can be mounted on the listening device 110 over the proximity sensor 610. The hood 704 can be a rubber sleeve, cap, or film formed to have a shape of the portion of the listening device 110 that fits into a user's ear. For example, the shape and size of the rubber earpiece hood 704 can be selected based on the need to conform to the size and shape of the upper body segment of the listening device 110. The hood 704 can provide a reflection surface adjacent to the proximity sensor 610. After installing the earpiece hood 704, the proximity sensor 610 can receive the necessary signal feedback for the earpiece software to activate/enable the full functionality of the earpiece, such as enabling the microphone 206. The earpiece hood 704 allows the software being run on the listening device 110 and/or the mobile device 108 to determine that the listening device 110 is being used in a use case that requires the microphone 206 to be active.

Figure 8:
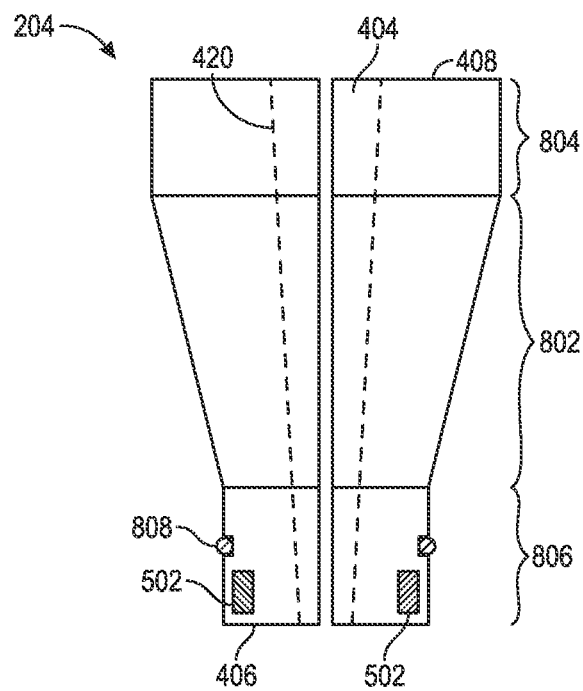
FIG. 8 is a sectional view of an adaptor of a self-auscultation device, in accordance with an embodiment.

Referring to FIG. 8, a sectional view of an adaptor of a self-auscultation device is shown in accordance with an embodiment. In an embodiment, the adaptor 204 can have a segmented outer profile. The segmented outer profile can include one or more tapered segments and one or more cylindrical segments. For example, the segmented outer profile may include a tapered segment axially between a proximal cylindrical segment 804 and a distal cylindrical segment 806.

The segmented earpiece adaptor 204 can adapt an off-the-shelf Bluetooth earpiece to be securely installed and fully functional for the application of recording self-auscultation sounds. The upper, proximal cylindrical segment 804 can include a volume with a cylindrical outer wall with an inner wall compliant with the shape of the earpiece being adapted. The middle, tapered segment 802 comprises a volume with a conical-shaped outer wall that has an inner wall also compliant with the shape of the earpiece being adapted. The lower, distal cylindrical segment 806 comprises a volume with a cylindrical outer wall and an inner wall compliant with the shape of the earpiece being adapted. The inner wall of the segments can define the adaptor channel 404 that has the profile 420 conforming to and compliant with the shape of the earpiece. If the length of the microphone boom 606 of the listening device 110 is shorter than the functional length of the segmented earpiece adaptor 204 the interior wall of the middle or lower segments may be configured as a cylindrical wall between the end of the microphone boom 606 and the distal adaptor end 406.

Notably, the upper segment of the adaptor 204 provides a member that performs a handle function as the adaptor 204 is inserted or removed from the chest piece 202. The middle segment of the adaptor 204 provides stability to the mounting of the wireless earpiece, as it can be compressed by a corresponding wall of the chest piece 202. The lower segment can include an adaptor seal 808, e.g., an O-ring, that seals against the chest piece 202 within the chest piece channel 306 and maintains an air tight concavity 302 to ensure maximum sound wave power reaches the microphone 206. Additionally, as described above, when the integrated adaptor magnets 502 are installed in the lower segment of the segmented adaptor 204, the chest piece magnets 324 provide retentive forces to help ensure the segmented adaptor 204 remains securely in the segmented adaptor port.

Figure 9:
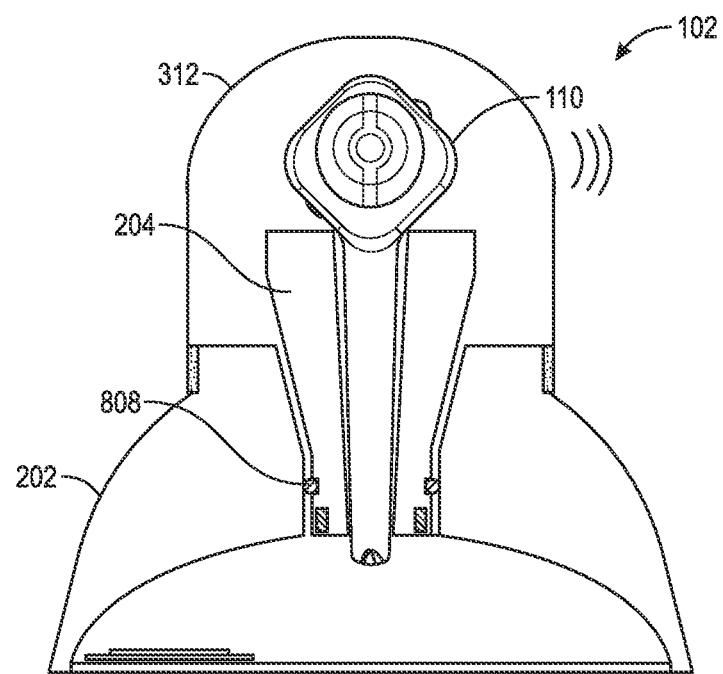
FIG. 9 is a sectional view of a self-auscultation device, in accordance with an embodiment.

Referring to FIG. 9, a sectional view of a self-auscultation device is shown in accordance with an embodiment. The segmented adaptor 204 is shown mounted in the chest piece 202. The chest piece 202 includes an interior surface that conforms to an exterior surface of the adaptor 204. For example, the chest piece channel 306 can have a tapered segment and a cylindrical segment, mirroring corresponding segments of the adaptor 204. Accordingly, as in the embodiments described above, an interior surface of the chest piece 202 defining the chest piece channel 306 can conform to an exterior surface of the adaptor 204 when the adaptor is mounted within the chest piece channel 306. The self-auscultation device 102 having the segmented adaptor 204 may therefore include components having similar structure and function as those described above with respect to FIGS. 2-7.

Figure 10:
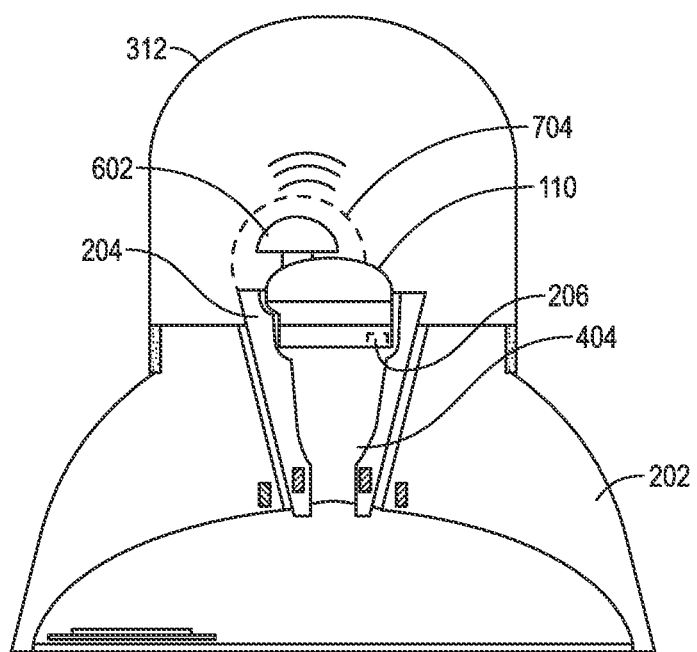
FIG. 10 is a sectional view of a self-auscultation device, in accordance with an embodiment.

Referring to FIG. 10, a sectional view of a self-auscultation device is shown in accordance with an embodiment. In an embodiment, the listening device 110 is an earbud-type earphone 600. In the case of an earbud, the listening device 110 may not include the microphone boom 606. The self-auscultation device 102 can include similar components as those described above with respect to FIGS. 2-9, however, the adaptor 204 may include a structure particularly adapted to the earbud. More particularly, the inner surface of the adaptor 204 defining the adaptor channel 404 can be shaped to conform to an outer envelope of the earbud. For example, the inner surface can have a segmented profile with regions of different cross-sectional dimensions that conform to the size of the earbud. Accordingly, an adaptor 204 may be used to fit a particular model of listening device 110, whereas a generic chest piece 202 may be used having a chest piece channel 306 to receive all different models of adaptors 204. This can allow the patient 104 to use the chest piece 202 with a variety of listening devices 110 by simply swapping out the adaptors 204.

An assembly procedure for the self-auscultation device 102 is briefly described below. The user can assemble the self-auscultation device 102 by first obtaining the chest piece 202, the listening device 110, the adaptor 204 compatible with the listening device 110, the cap 312, and the hood 704. The listening device 110 can be assembled into the adaptor 204. The listening device 110 and adaptor 204 combination can be inserted into the chest piece channel 306, e.g., an adaptor port, of the chest piece 202. The listening device 110 can be turned on. The hood 704 can be installed over the proximity sensor 610 of the listening device 110. The cap 312 can be installed onto the chest piece 202. The self-auscultation device 102 may then be assembled and ready for use in a self-auscultation method.

Figure 11:
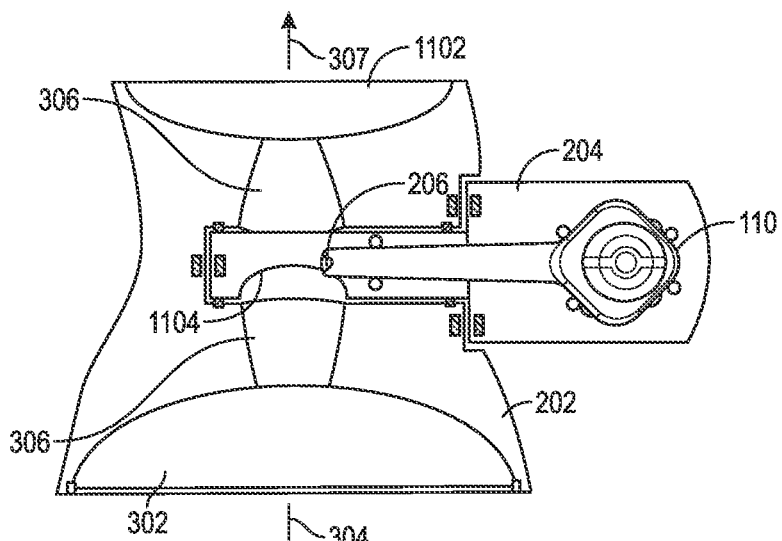
FIG. 11 is a sectional view of a self-auscultation device, in accordance with an embodiment.

Referring to FIG. 11, a sectional view of a self-auscultation device is shown in accordance with an embodiment. The self-auscultation device 102 can be a dual-bell-type self-auscultation device. In an embodiment, the chest piece 202 includes two bells, e.g., the concavity 302 facing the first direction 304 and a second concavity 1102 facing the second direction 307. Accordingly, whereas sound can enter the chest piece channel 306 through the concavity 302 in a one direction, sound can enter the chest piece channel 306 through the second concavity 1102 in another, e.g., opposite, direction. More particularly, either side of the chest piece 202 can be pressed against the chest to self-auscultate the target anatomy.

In an embodiment, the concavities are differently sized. For example, the concavity 302 can have a larger volume than the second concavity 1102. The smaller concavity 302 can be used to listen to lower frequency sounds from the patient 104's chest wall, as compared to sounds that the larger concavity 302 is used to listen to. Accordingly, the user can select between listening to either the large bell or the small bell during the self-auscultation procedure. The small bell may also auscultate contact points on the human chest that have constrained access due to bones surrounding that point.

Figure 18:
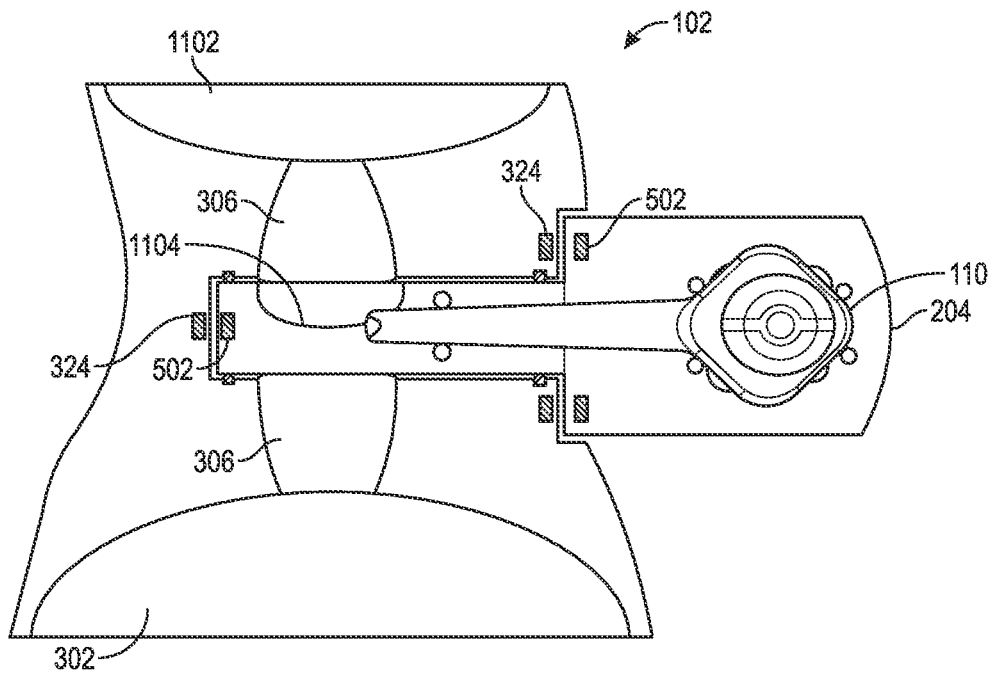
FIG. 18 is a sectional view of a self-auscultation device, in accordance with an embodiment.

The adaptor 204 can be inserted into the chest piece 202 in a direction transverse to the central axis extending through the concavities. More particularly, the adaptor 204 can extend transversely through the chest piece channel 306. The adaptor 204 can be rotatable between a first configuration (FIG. 11) and a second configuration (FIG. 18). In the first configuration, a space within the adaptor, e.g., an adaptor recess 1104, can be placed in fluid communication with the first concavity 302 (and not the second concavity 1102). By contrast, in the second configuration, the adaptor recess 1104 can be placed in fluid communication with the second concavity 1102 (and not the concavity 302).

The listening device 110 can be supported by the adaptor 204 within the chest piece 202. In an embodiment, the microphone 206 of the listening device 110 is exposed to the adaptor recess 1104. Accordingly, the microphone 206 can detect sounds received through the concavity 302 in the first configuration, and the microphone 206 can detect sounds received through the second concavity 1102 when the adaptor 204 is rotated into the second configuration.

Figure 12:
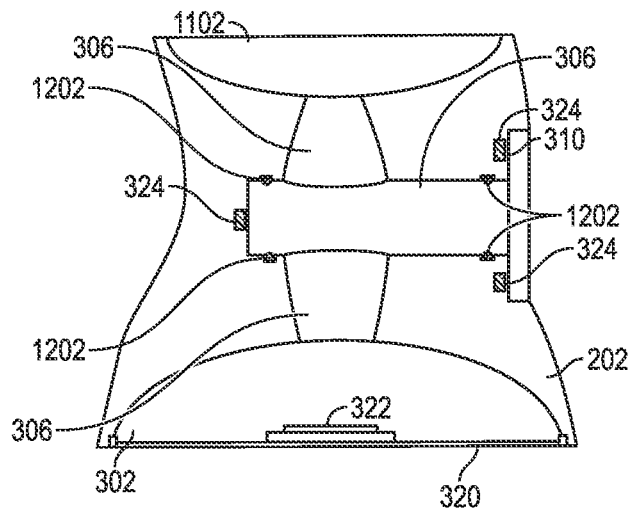
FIG. 12 is a sectional view of a chest piece of a self-auscultation device, in accordance with an embodiment.

Referring to FIG. 12, a sectional view of a chest piece of a self-auscultation device is shown in accordance with an embodiment. The concavities and the chest piece channel 306 can be in fluid communication with a surrounding environment. As shown, the chest piece channel 306 can extend vertically between the concavities, and can also extend horizontally toward the mounting wall 310 used to receive the adaptor 204. More particularly, a recess can be formed in a side surface of the chest piece 202 to receive the adaptor 204. One or more chest piece magnets 324 can be embedded within the chest piece 202, adjacent to the mounting wall 310 and/or adjacent to a lateral end of the chest piece channel 306 within the chest piece body. The chest piece magnets 324 can interact with corresponding adaptor magnets 502 to retain the adaptor 204 within the chest piece 202 during use.

In an embodiment, the chest piece 202 can include one or more chest piece seals 1202 to seal against the adaptor 204 when it is inserted into the chest piece channel 306. The chest piece seals 1202 can be O-rings that seal circumferentially around the adaptor 204 such that the adaptor recess 1104 is longitudinally between the seals. The seals provide smooth rotational operation of the adaptor 204. The seals can create an air tight auscultation chamber. More particularly, the seals can seal off the chest piece channel 306 to create a closed path between the concavity 302 (or the second concavity 1102) and the adaptor recess 1104. The seals may also secure the rotatable encapsulation adaptor 204 to prevent extraneous mechanical noises from being injected into the health sound recording. More particularly, the chest piece seals 1202 may provide acoustic damping to the system.

Figure 13:
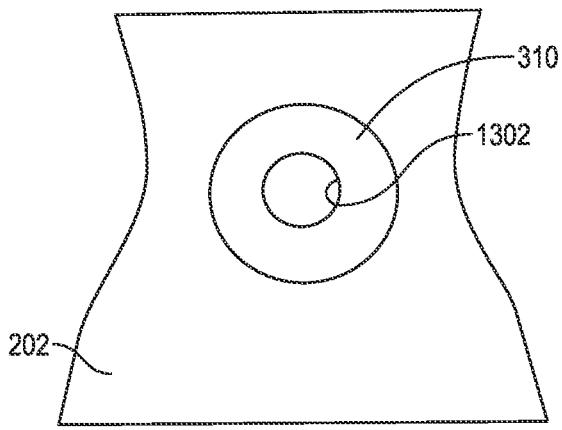
FIG. 13 is a side view of a chest piece of a self-auscultation device, in accordance with an embodiment.

Referring to FIG. 13, a side view of a chest piece of a self-auscultation device is shown in accordance with an embodiment. The side view illustrates a view into the adaptor port 1302 in the side surface of the chest piece 202.

The adaptor port 1302 can be located central to the mounting wall 310 that the adaptor 204 mounts on when it is inserted into the chest piece 202. More particularly, the adaptor port 1302 can receive the adaptor 204 containing the listening device 110. When the adaptor 204 is located in the adaptor port 1302, it can hold the microphone 206 of the listening device 110 in a position to maximize the acoustic performance required to record high fidelity auscultation audio data.

Figure 14:
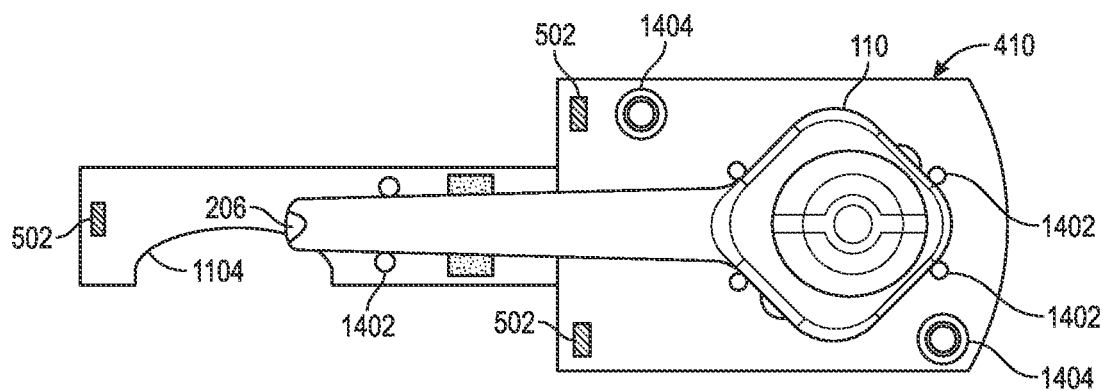
FIG. 14 is side view of a first portion of an adaptor of a self-auscultation device, in accordance with an embodiment.
Figure 15:
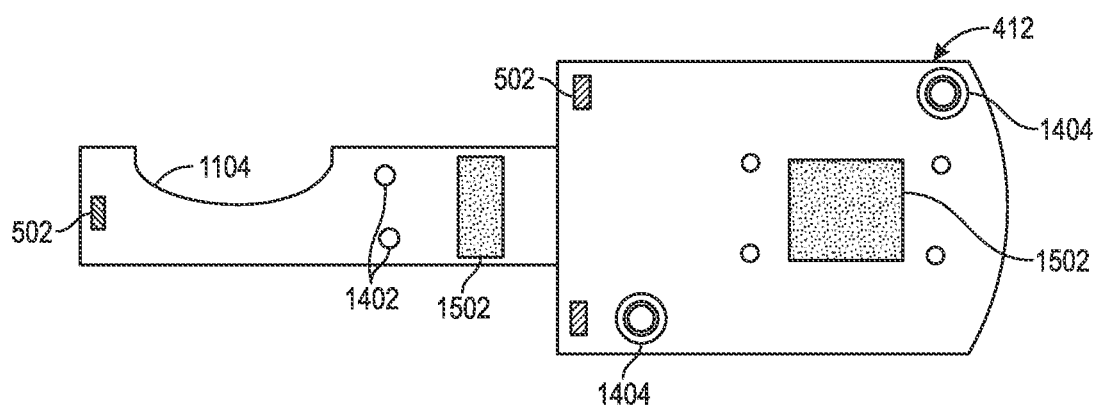
FIG. 15 is side view of a second portion of an adaptor of a self-auscultation device, in accordance with an embodiment.

Referring to FIG. 14, a side view of a first portion of an adaptor of a self-auscultation device is shown in accordance with an embodiment. The adaptor 204 can include several portions. For example, the adaptor 204 can be formed in two halves, e.g., a first adaptor portion 410 and a second adaptor portion 412 (FIG. 15). The adaptor portions can include internal features to provide positional control and to support the listening device 110. For example, the adaptor portions can include positioning posts 1402 that can fit around an outer surface of the listening device 110 to hold the device in place. The adaptor portions can also include screw bosses 1404 that can be used to secure the first adaptor portion 410 to the second adaptor portion 412 (FIG. 15). The screw bosses 1404 can engage holes on an opposing part for positional control, and can receive screws to secure the portions together.

The adaptor portions can include a directional audio port. More particularly, the adaptor portions can include the adaptor recess 1104, which can provide the directional audio port. The directional audio port can receive and direct self-auscultation health sounds to the microphone 206 of the listening device 110.

Referring to FIG. 15, a side view of a second portion of an adaptor of a self-auscultation device is shown in accordance with an embodiment. The second adaptor portion 412 can mirror the first adaptor portion 410. For example, the adaptor recess 1104 of the second adaptor portion 412 can mirror the adaptor recess 1104 of the first portion to form the directional audio port. Similarly, the positioning posts 1402 and the screw bosses 1404 (or holes) on the second adaptor portion can mirror those on the first adaptor portion such that the corresponding components engage when the adaptor portions are assembled and combined to form the adaptor 204.

In an embodiment, the adaptor portions include one or more foam pads 1502. The foam pads 1502 can be adhered to the adaptor portions with adhesive bonds. The foam pads 1502 can be positioned such that they press against the listening device 110 to secure and cushion the listening device 110 against movement when the adaptor 204 is inserted into the chest piece 202.

Figure 16:
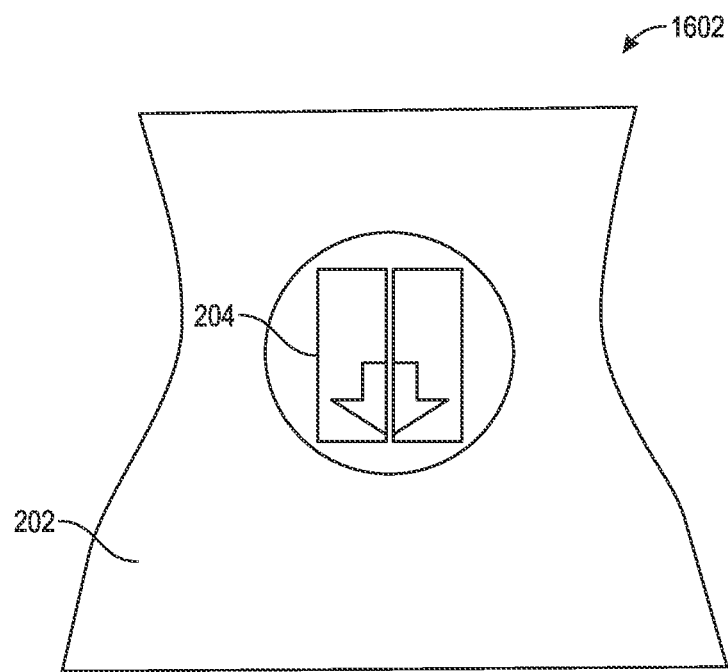
FIG. 16 is a side view of a self-auscultation device having an adaptor in a first configuration, in accordance with an embodiment.

Referring to FIG. 16, a side view of a self-auscultation device having an adaptor in a first configuration 1602 is shown in accordance with an embodiment. A proximal region of the adaptor 204 that extends laterally from the side surface of the chest piece 202 can be held and turned like a knob. When the knob is rotated to direct the directional audio port downward (indicated by the arrow), the microphone 206 of the listening device 110 within the adaptor 204 can be placed in fluid communication with the concavity 302 to collect sounds from the large bell.

Figure 17:
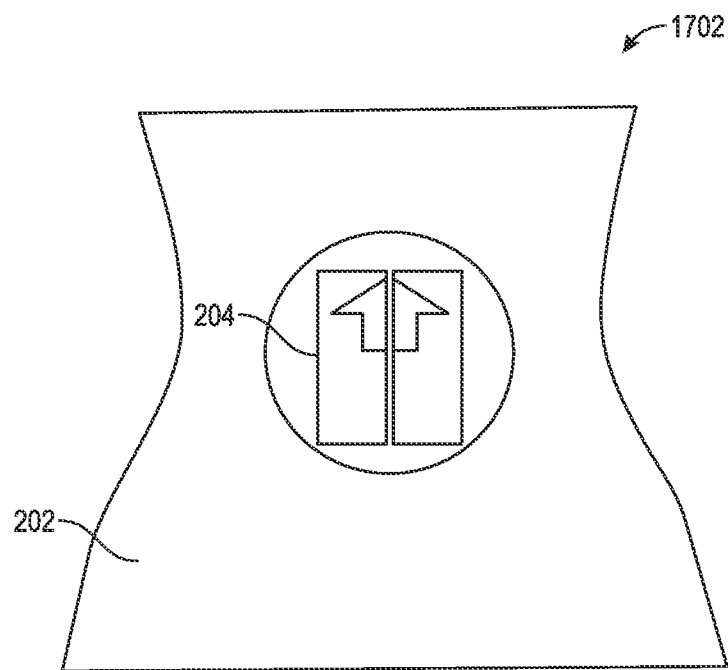
FIG. 17 is a side view of a self-auscultation device having an adaptor in a second configuration, in accordance with an embodiment.

Referring to FIG. 17, a side view of a self-auscultation device having an adaptor in a second configuration is shown in accordance with an embodiment. The adaptor knob can be rotated to a second configuration 1702 to direct the directional audio port upward (indicated by the arrow). In the second configuration 1702, the microphone 206 of the listening device 110 within the adaptor 204 can be placed in fluid communication with the second concavity 1102 to collect sounds from the small bell.

Referring to FIG. 18, a sectional view of a self-auscultation device is shown in accordance with an embodiment. In the sectional view, the adaptor 204 is shown rotated into the second configuration 1702 such that the adaptor recess 1104 is in fluid communication with the portion of the chest piece channel 306 between the second concavity 1102 and the adaptor 204. The chest piece magnets 324 and the adaptor magnets 502 can interact to retain the adaptor 204 in the second configuration 1702. Similarly, when the adaptor 204 is rotated into the first configuration 1602, the magnets can interact to maintain the adaptor position. Accordingly, the magnets can be used both for retention of the adaptor 204 within the chest piece 202 and to control the rotational position of the adaptor 204 within the chest piece 202.

Figure 19:
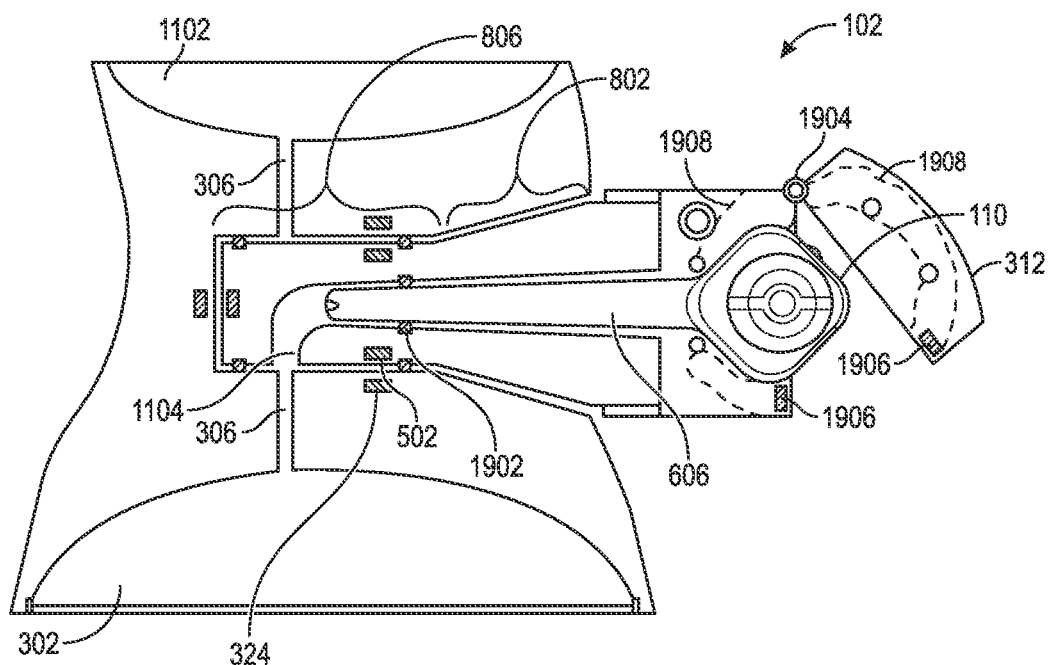
FIG. 19 is a sectional view of a self-auscultation device, in accordance with an embodiment.

Referring to FIG. 19, a sectional view of a self-auscultation device is shown in accordance with an embodiment. Like the single-bell configuration, the dual-bell configuration of the self-auscultation device 102 may also employ a segmented adaptor 204. More particularly, the adaptor 204 can include one or more tapered section and one or more cylindrical section. For example, the tapered section 802 can be proximal to the distal cylindrical segment 806.

In an embodiment, the chest piece magnets 324 and the adaptor magnets 502 are located around the distal cylindrical segment 806. The magnets can be offset, e.g., by 180 degrees, such that they interact in both the first configuration 1602 and the second configuration 1702. Accordingly, the adaptor 204 can be rotated to direct the adaptor recess 1104 toward a corresponding concavity. As shown, the adaptor recess 1104 can be a channel that aligns with corresponding chest piece channels 306. The chest piece channels 306 can place the adaptor recess 1104 in fluid communication with the concavities to allow sound to propagate from the bells to the microphone 206.

FIG. 19 illustrates several optional features, which like the other features described herein, may be incorporated in any of the self-auscultation device 102 embodiments. The self-auscultation device 102 can include one or more boom seals 1902. The boom seal 1902 can be a seal, such as an O-ring, that extends around the microphone boom 606 to seal a channel between the listening device 110 and the adaptor 204. More particularly, the seal can block the space between the components to prevent acoustic leakage, and thus, to improve audio performance of the self-auscultation device 102. It will be appreciated that the boom seal 1902 may also secure and stabilize the listening device 110 within the adaptor 204.

In an embodiment, the self-auscultation device includes a hinged cap 312. The cap 312 can have several portions that are hinged together at a hinge 1904, or alternatively, the cap can be hinged directly to the adaptor 204 at the hinge 1904. The hinged cap 312 can be opened and closed easily, to allow a user to insert and/or remove the listening device 110 from the adaptor 204. Closure of the hinged cap 312 can be secured by cap magnets 1906, which interact magnetically to hold the portions of the cap (or the cap and the adaptor) together in a closed state.

The hinged cap 312 can incorporate a cap hood 1908. The cap hood 1908 can function similar to the hood 704, however, it may be built directly into the cap 312. For example, the cap hood 1908 can include foam inserts that are positioned within the cap 312 such that, when the listening device 110 is inserted into the adaptor 204 and the cap 312 is in the closed state, the cap hood 1908 can cover the proximity sensor 610. The cap hood 1908 can also press against the in-ear portion of the listening device 110 to secure and stabilize the component within the self-auscultation device 102.

Having discussed several embodiments of the self-auscultation device 102, which conduct sounds from a target anatomy to a readily available, off-the-shelf earphone, the description shall now turn to the use of the self-auscultation device 102 as part of a system used for performing a method of self-auscultation.

Figure 20:
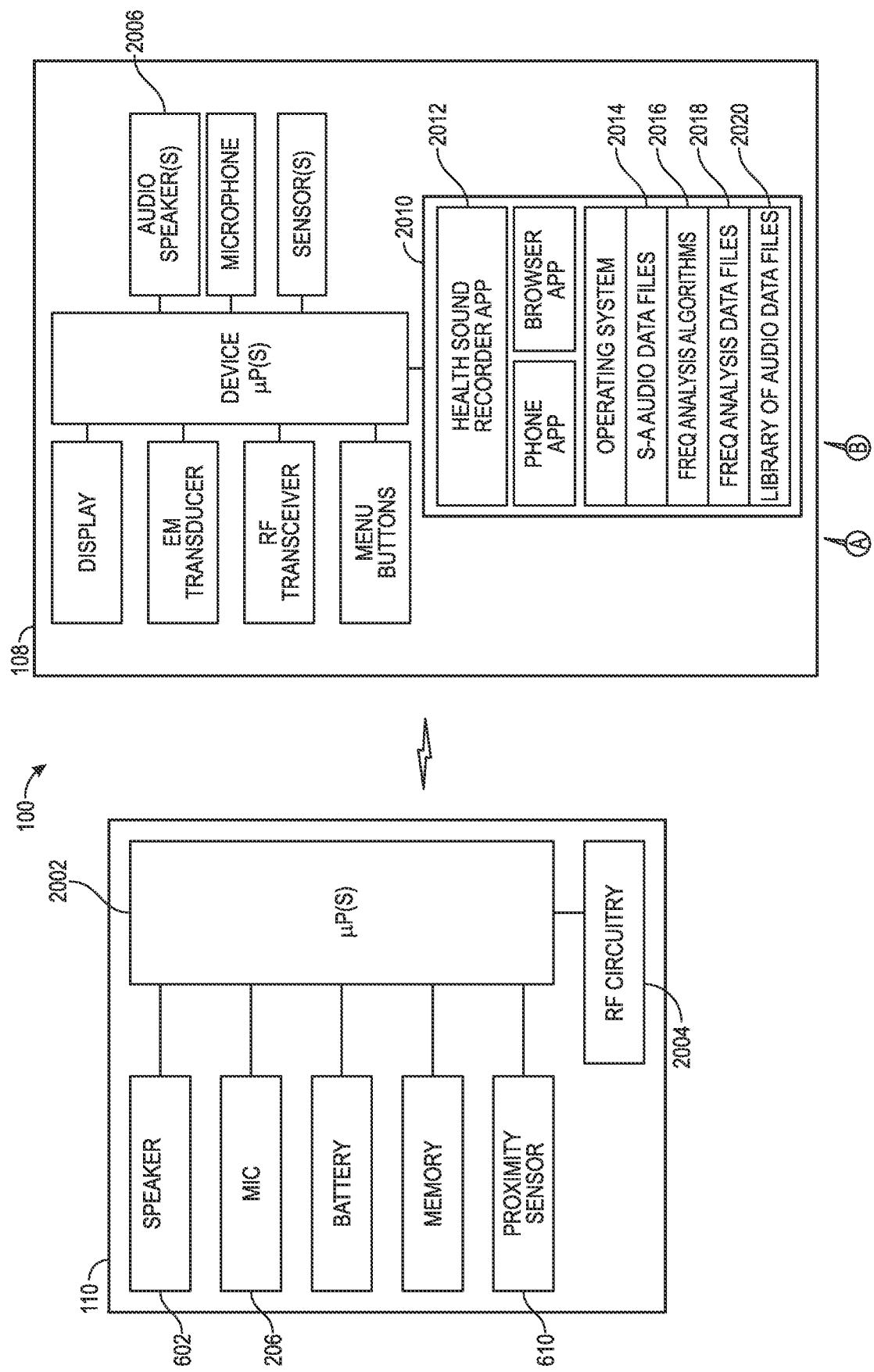
FIG. 20 is block diagram of a remote health monitoring system, in accordance with an embodiment.
Figure 20:
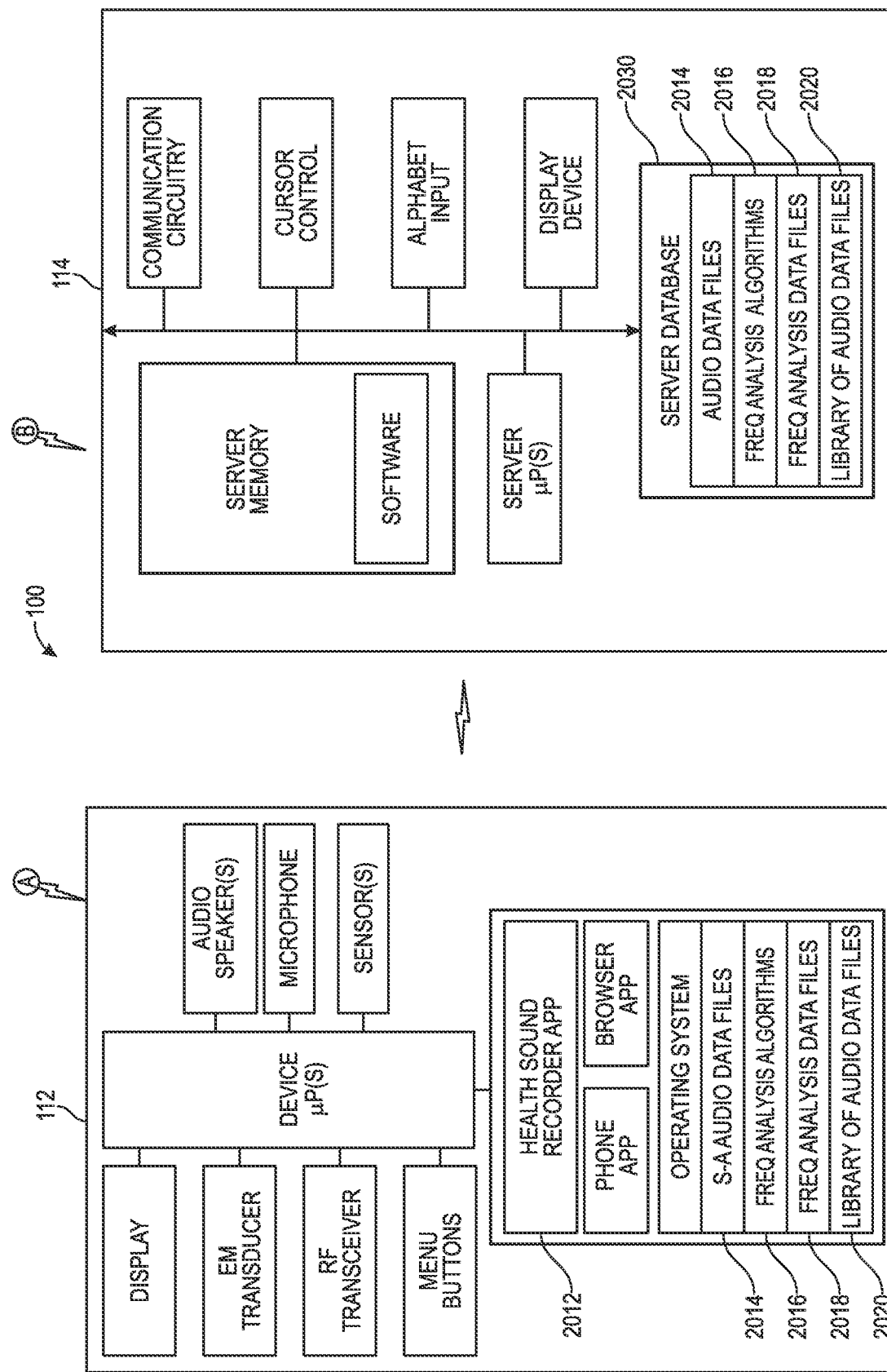

Referring to FIG. 20, a block diagram of a remote health monitoring system is shown in accordance with an embodiment. The remote health monitoring system 100 can include the listening device 110 and one or more of the mobile device 108, the healthcare provider device 112, or the remote server 114. When fully assembled, the self-auscultation device 102 can be paired with the mobile device 108 of the patient 104. More particularly, the listening device 110 held by the self-auscultation device 102 can be paired with the mobile device 108.

The listening device 110 can include a housing containing several components suited to the purpose of performing the self-auscultation method described below. One or more processors 2002 of the listening device 110 can execute instructions stored on a non-transitory computer readable medium (memory) to perform the method of self-auscultation. The one or more processors 2002 can be electrically connected with other components to receive or send signals. For example, the one or more processors 2002 can be connected to the proximity sensor 610 to detect proximity to an ear (or to the hood 704) in order to enable and receive audio signals from the microphone 206 of the listening device 110. The audio signals can correspond to sounds detected by the microphone 206, and the one or more processors 2002 can process the audio signals to generate audio data. Similarly, the one or more processors 2002 can be connected to the earphone speaker 602 to output audio when the listening device 110 is being used by the patient 104 as an earphone (as opposed to being used as a self-auscultation component). The listening device 110 may also include RF circuitry 2004, e.g., the low power Bluetooth radio, used to transmit audio data to the mobile device 108, receive firmware configuration commands from the mobile device 108, or transmit/receive any other data between the listening device 110 and the mobile device 108.

The mobile device 108, which may be paired with the listening device 110, similarly includes components to perform the method of self-auscultation. The mobile device 108 may be a smartphone or a tablet computer, and may have components germane to such devices. For example, the mobile device 108 can include a display, menu buttons, or any of the other illustrated components. The components can include input devices, such as a microphone or various sensors. The mobile device 108 may also include output devices, such as an audio speaker 2006 to produce output tones, such as the test tones described below. The mobile device 108 can include RF circuitry, e.g., one or more RF transceivers, to communicate signals with the listening device 110, the healthcare provider device 112, or the remote server 114.

In an embodiment, the mobile device 108 includes one or more processors to execute instructions stored on a non-transitory computer readable medium 2010. The stored instructions can include applications, such as a telephony application, a browser application, etc. The applications may also include the health sound recorder application 2012 described below. The applications can run on an operating system of the mobile device 108. The applications may have access to stored data. For example, the health sound recorder application can access self-auscultation audio data files 2014, frequency analysis algorithms 2016, frequency analysis data file 2018, and a library of audio data files 2020, all of which are described in further detail below.

The health sound recorder application in combination with the operating system of the mobile device 108 can be responsible for establishing, managing, and ending the wireless link between the listening device 110 and the mobile device 108. The health sound recorder application will periodically monitor parameters that show the hardware status of the listening device 110, including: received signal strength indicator (RSSI) for Bluetooth signal strength, current battery level, or other parameters indicating device status.

The mobile device 108 can communicate with the healthcare provider device 112 over communication channels. The healthcare provider device 112 can be a mobile phone, a tablet or desktop computer, or another data processing system. The healthcare provider device 112 can include components similar to those of the mobile device 108 in order to receive and process information. For example, the healthcare provider device 112 can receive self-auscultation audio data from the mobile device 108 to remotely monitor the patient 104. The healthcare provider device 112 can have memory, similar to memory 2010 of the mobile device, storing the health sound recorder application 2012.

The mobile device 108 or the healthcare provider device 112 can communicate with the remote server 114. The remote server 114 can include components to perform the self-auscultation method. The remote server 114 can be a data processing system having server memory storing software, one or more server processors, communication circuitry to communicate with other devices, and user interface devices, such as a cursor control, alphanumeric input device, or display device.

The remote server 114 can include a server database 2030 storing data for the self-auscultation method. For example, the server database 2030 can store the self-auscultation data files 2014, frequency analysis algorithms 2016, frequency analysis data files 2018, or library of audio data files 2020. The remote server 114 may therefore store and/or process self-auscultation data, and communicate the data to the healthcare provider 106 for remote monitoring of the patient 104.

A method of performing self-auscultation using the remote health monitoring system 100 is described below with respect to FIGS. 21-24. It will be appreciated that the operations and sub-operations described may be performed by more than one of the system components. For example, audio data processing can be performed at the mobile device 108, the healthcare provider device 112, or the remote server 114. Accordingly, it will be appreciated that any of the operations may be performed by any of the system components described above, and their description as being performed by a specific component is not limiting.

Figure 21:
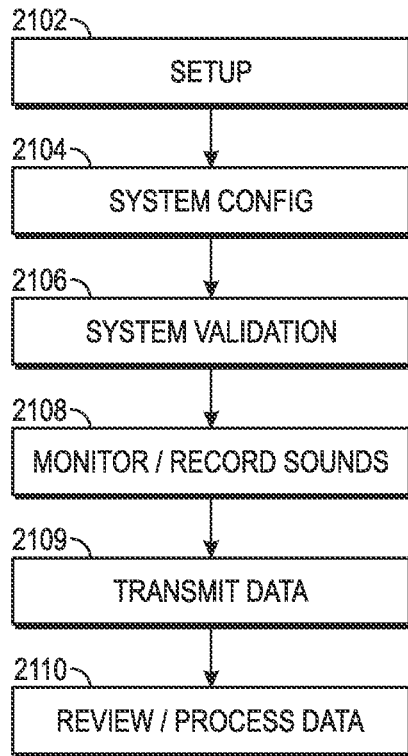
FIG. 21 is a flowchart of a method of performing self-auscultation using a self-auscultation device, in accordance with an embodiment.
Figure 22:
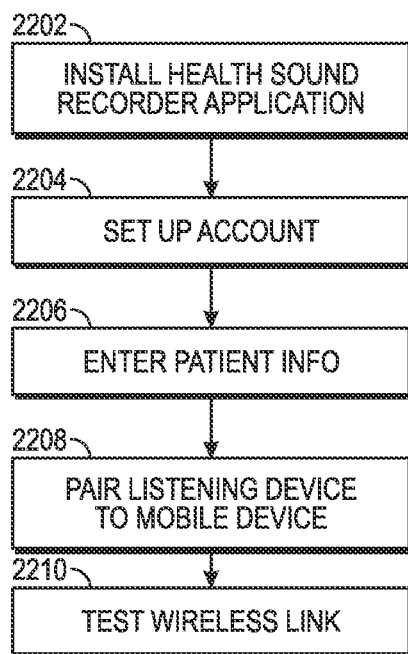
FIG. 22 is a flowchart of a method of setting up a self-auscultation device, in accordance with an embodiment.

Referring to FIG. 21, a flowchart of a method of performing self-auscultation using a self-auscultation device is shown in accordance with an embodiment. At operation 2102, the system can setup the system device(s) to perform the method of self-auscultation. Referring to FIG. 22, a flowchart of a method of setting up a self-auscultation device is shown in accordance with an embodiment. The functional sequence can be executed by the software of the mobile device 108 during a system setup mode. The health sound recorder application 2012 can be downloaded from an on-line application store, and installed on the mobile device 108, e.g., a smartphone or tablet computer of the patient 104. At operation 2202, upon first running the health sound recorder application 2012, the software will boot directly into a setup mode. At operation 2204, the patient 104 will set up an account on the remote server 114, which may be administered by their healthcare provider 106. At operation 2206, the patient 104 continues the setup process by entering their personal information. The personal information can include: name, age, sex, email address, medical insurance, healthcare provider, etc. At operation 2208, the operating system of the mobile device pairs the mobile device 108 with the listening device 110. The listening device 110 can be mounted or otherwise installed within the self-auscultation device 102, and thus, the mobile device 108 may be "paired" with the self-auscultation device 102. At operation 2210, after the wireless, e.g., Bluetooth, pairing is complete, the health sound recorder application 2012 will perform a test by reading the current battery level of the listening device 110. The battery test can confirm that the mobile device 108 can communicate with the wireless earpiece, e.g., that the devices are in wireless communication and/or that the listening device 110 has adequate charge to perform the self-auscultation method. The health sound recorder may also perform a test to verify that the current version of firmware in the Bluetooth earpiece is actually the latest version of firmware. If needed, the health sound recorder application can perform a firmware update of the listening device 110 to upgrade the listening device 110 to the latest firmware version, if needed.

Other methods of performing the sequence of sub-operations of the setup operation are contemplated. For healthcare providers 106 who have an internal IT department, the provider may choose to pre-install and pre-configure the health sound recorder application 2012 and/or firmware on the mobile device 108 and/or listening device 110 prior to providing the device(s) to the patient 104. Alternatively, the IT department could support the setup tasks by providing a set of QR codes to simplify the installation of the mobile application software by allowing the patient 104 to scan a QR code that allows them to download the health sound recorder application 2012. Also the setup data of the patient can be automatically uploaded into the mobile application by scanning a QR code that links to a secure database administered by the IT department of their healthcare provider 106.

Figure 23:
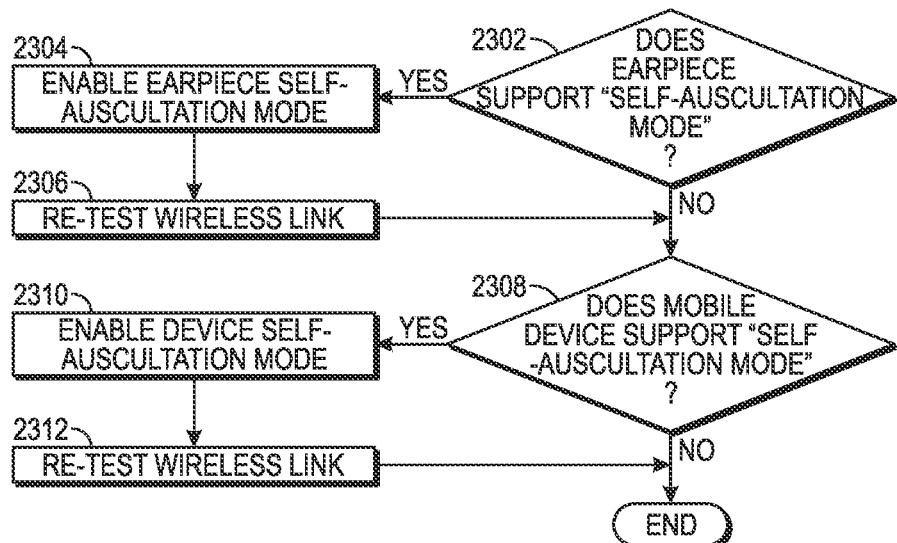
FIG. 23 is a flowchart of a method of adapting a device to be used in a self-auscultation mode, in accordance with an embodiment.

Referring again to FIG. 21, at operation 2104, the system performs a system configuration procedure. Referring to FIG. 23, a detailed flowchart of a method of adapting a device to be used in a self-auscultation mode is shown in accordance with an embodiment. The remote health monitoring system 100 can determine whether a device is being used for self-auscultation of a target anatomy. For example, one or more processors can determine that the mobile device 108 and/or the listening device 110 is being used for self-auscultation when the patient 104 launches the health sound recorder application 2012. The system can determine whether the devices, e.g., the listening device 110 or the mobile device 108, support a self-auscultation mode. The listening device 110 may support firmware functions including the auscultation mode that allows the health sound recorder application 2012 to set the listening device 110 into an application-specific mode that includes specific settings that optimize the listening device 110 for being used in the self-auscultation device 102 to monitor heart or lung sounds.

At operation 2302, the health sound recorder application 2012 can query the listening device 110 to determine whether the self-auscultation mode is supported. If the listening device 110 supports the mode, at operation 2304, the self-auscultation mode is enabled on the listening device 110. The health sound recorder application can access an API and enable the self-auscultation mode in the listening device firmware. If no API is available but the listening device 110 does support self-auscultation mode, the health sound recorder application 2012 can instruct/prompt the user to go to the Bluetooth settings menu on their computing device and manually enable the self-auscultation mode for the listening device 110. At operation 2306, the wireless link between the mobile device 108 and the listening device 110 may again be tested, e.g., by checking a battery status of the listening device 110.

At operation 2302, if the listening device 110 does not support the mode, the system may advance to operation 2308, at which the health sound recorder application 2012 can determine whether the mobile device 108 supports the self-auscultation mode. If the mobile device 108 supports the mode, at operation 2310, the self-auscultation mode is enabled on the mobile device 108. At operation 2312, the wireless link between the mobile device 108 and the listening device 110 may again be tested, e.g., by checking a battery status of the listening device 110.

When it is determined that either the mobile device 108 or the listening device 110 are being used for self-auscultation of the target anatomy, and/or when it is determined that the self-auscultation mode is supported on either the listening device 110 (operation 2302) or the mobile device 108 (2308), the respective device can be set to operate in the self-auscultation mode.

Configuring the device to operate in the self-auscultation mode can include setting one or more device configuration settings. For example, one or more of a microphone configuration, a voice activation configuration, a noise cancellation configuration, a voice assistant configuration, a battery usage configuration, a proximity sensor configuration, a Bluetooth transmission protocol configuration, an incoming call mute configuration, an incoming notification mute configuration, or a device pairing configuration can be set for the listening device 110 or the mobile device 108.

A microphone configuration can include increasing a microphone gain setting of the microphone 206, e.g., by setting it to a maximum level or a level higher than normal. The microphone configuration can also include disabling any feature supporting the variability of the microphone gain based on background noise levels. The microphone gain configuration can also include increasing the audio data sampling rate in the Analog to Digital convertor chip in listening device 110 to improve the fidelity of the audio data recorded. The microphone configuration can also include setting a frequency response characteristics of the microphone 206. For example, the self-auscultation mode can support advanced configurations that include settings for altering the frequency response characteristics of the amplification provided by the listening device 110. These advanced settings to alter the frequency response may be assigned modes specific to the target anatomy. For example, the frequency response setting used to auscultate the heart valves can isolate and amplify the most important frequency content of the sound waves generated by the valves in the heart. Similarly, the listening device firmware may include an auscultation mode configuration for frequencies specific to the heart muscle or lung function.

A voice activation configuration can include disabling voice activation. For example, the voice activation configuration for self-auscultation mode can include disabling the voice activation feature of any application installed on the mobile device 108 with the exception of the health sound recorder application 2012. More particularly, the voice activation configuration may include disabling voice activation for all applications installed on the mobile device 108 except the health sound recorder application 2012. Disabling the voice activation of non-essential application(s) during the monitoring and recording of health sounds can ensure the most reliable user experience and the most accurate collection of audio data.

A noise cancellation configuration can include disabling noise cancellation. The noise cancelation configuration can include defeating the functionality within listening device 110 to monitor for perceived background noises received into microphone 206 and then subtract those sounds out of the audio data content available to be recorded. As such, active noise cancelation may alter and corrupt the auscultation audio data files recorded by the health sound recorder application 2012.

A voice assistant configuration can include disabling a voice assistant. The voice assistant configuration can include disabling this functionality to ensure that the voice assistant does not accidentally identify a word spoken by the user as a command. Such accidental identification can cause the voice assistant to inadvertently respond with audio output or take other action. Such voice assistant interruptions may potentially alter and corrupt the auscultation audio data files recorded by the health sound recorder application 2012.

A battery usage configuration can include setting a battery saving mode to an off configuration. More particularly, the listening device 110 and/or the mobile device 108 can be set to prioritize data fidelity and data transmit performance over settings intended to minimize power consumption. Listening devices are typically constrained in the size of their battery to fit a very streamlined form factor and as such they are typically provided to consumer, or "shipped," with all power save modes enabled. During important health-focused self-auscultation procedures there is a justified need to prioritize the configuration of the listening device 110 to maximize the fidelity of the audio data collected over any need to obtain battery energy savings.

A proximity sensor configuration can include setting the in-ear proximity sensor 610 to an off, or disabled, configuration. More particularly, the in-ear proximity sensor 610 of the listening device 110 can be turned off. Typically, when listening device 110 is equipped with an in-ear proximity detector, the firmware of the device will attempt to save battery power by disabling the microphone of the earphone when the proximity detector is not activated. In the embodiments of FIG. 7 and FIG. 10, the functionality of hood 704 is shown to provide a means of activating the proximity sensor of listening device 110 to allow for microphone to become and remain active. The hood 704 component can be intended as a solution for listening devices that do not have firmware capable of supporting self-auscultation mode.

A Bluetooth transmission protocol configuration can include setting the listening device 110 to use a Bluetooth wireless transmission protocol that uses more power and delivers reduced transmit range but more importantly provides greater channel bandwidth and/or data transmit capability for recording audio data files of higher audio fidelity. By selecting an alternate transmission protocol, the listening device firmware may enhance the bandwidth of a Bluetooth wireless connection to mobile device 108, thus achieving a performance advantage resulting in higher fidelity and accuracy in the resulting audio data files.

An incoming call mute configuration can include sending an incoming voice call directly to voice mail. An incoming call that comes in while the patient is performing an auscultation procedure to record health audio data files may disrupt the accurate collection of auscultation data. Accordingly, muting incoming calls can avoid such disruptions.

An incoming notification mute configuration can include disabling active notifications associated with the receipt of voice mail messages, text messages, or mobile applications. The audio chime tones associated with notifications may create a distraction while the patient is performing an auscultation procedure to record health audio data files and may disrupt the accurate collection of auscultation data. Accordingly, muting incoming notifications can avoid such distractions and disruptions.

A device pairing configuration can include enabling communication between the mobile device 108 and one or more pairs of listening devices in a particular configuration. The scope of possible configuration changes to support the self-auscultation mode can extend beyond settings in the listening device firmware to include special audio settings supported in the firmware of mobile device 108. For example, if the operating system of the smartphone supports the self-auscultation mode (as determined at operation 2308) the operating system can enable support for a configuration allowing the use of a second set of Bluetooth earpieces by the patient 104, rather than requiring them to set their smartphone to use 'speakerphone' to listen to the sounds being monitored by the listening device 110 in the self-auscultation device 102. Alternatively, a single set of Bluetooth earpieces could be supported by the smartphone operating system by allowing the splitting of a pair of Bluetooth earpieces in which a first earpiece of the pair is used in the self-auscultation device 102 to detect sounds and a second earpiece of the pair is used by the patient 104 to listen and monitor the sounds as they are performing the self-auscultation procedures.

The application-specific settings of the self-auscultation mode changes the listening device functionality and/or smartphone functionality to provide optimized functionality and audio performance specifically for the self-auscultation application. After setting the device(s) into the self-auscultation mode, the health sound recorder application 2012 can verify the wireless link is still functional by repeating the previous test to read the current battery level from the earpiece (operations 2306 and/or 2312).

Figure 24:
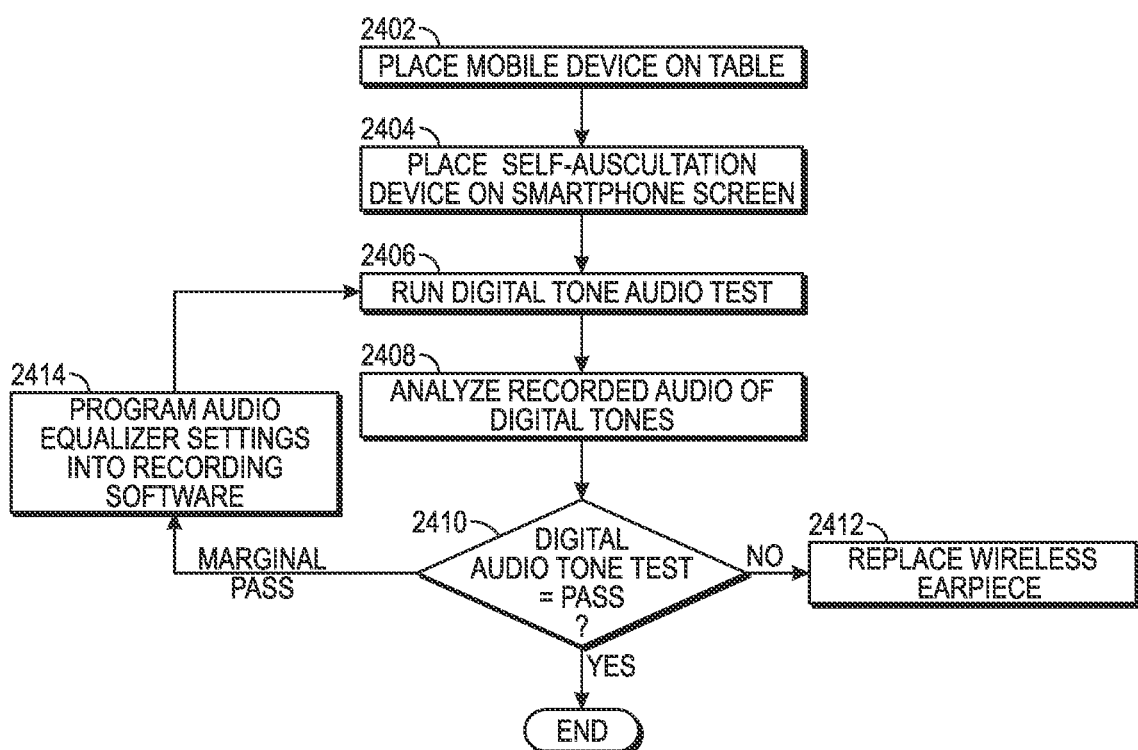
FIG. 24 is a flowchart of a method of validating a listening device to be used for self-auscultation mode, in accordance with an embodiment.

Referring again to FIG. 21, at operation 2106, the system can perform a system validation procedure. The validation procedure can verify the functionality of the self-auscultation device 102. Referring to FIG. 24, a flowchart of a method of validating a listening device 110 to be used for self-auscultation mode is shown in accordance with an embodiment. Ideally, the electronic components in the listening device 110 would provide both linear microphone transducer sensing and linear signal amplification of all human audible frequencies. That, however, is not always the case. Typically, less expensive Bluetooth earphones will have more non-linearity in the audio signals that the microphone sends to the Bluetooth radio frequency transmitter to be transmitted. To address potential issues with non-linear characteristics of the microphone 206 and amplification circuits, the health sound recorder application 2012 can test the frequency bandwidth characteristics of the listening device 110, and compensates for those characteristics if needed.

At operation 2402, the user can place the mobile device 108 on a table in a 'screen up' orientation and activate the validation procedure through a user interface of the health sound recorder application 2012. The user interface can then display a dashed outline of a circle on the screen. At operation 2404, the user may position the self-auscultation device 102 in a 'bell down' orientation on the screen of the smartphone within the dashed circular outline. After receiving a selection of a user interface element, e.g., "continue," the application can perform the linearity testing.

At operation 2406, a digital tone audio test is run by the mobile device 108 and the listening device 110. During the test, the mobile device 108 can emit one or more test tones. The test tones can be sounds emitted by the speaker 2006 of the mobile device 108.

The listening device 110 can detect the test tones. More particularly, a sensor of the listening device 110 can generate one or more test signals corresponding to the test tones emitted by the mobile device 108. The test signals can be audio data corresponding to audio signals generated by the microphone 206, for example.

At operation 2408, the health sound recorder application 2012 can evaluate the linearity of the listening device 110. During the evaluation, the test signals can be compared to the test tones. For example, frequency content of the digital audio data received from the listening device 110 can be compared with the known frequency content of the test tones output by the mobile device 108. More particularly, the frequency content of the test signals is compared to predetermined frequency content of the test tones, which is known because it is contained in the audio data file that the mobile device processor(s) use to drive the speaker 2006 to generate the test tones.

At operation 2410, the health sound recorder application 2012 can determine whether the digital audio tone test passes or fails. For example, if the comparison indicates that the test signals closely match the test tones, then the validation results can indicate a pass result. In such case, the frequency response of the listening device is acceptable and no audio equalizer settings are required for the listening device 110. Alternatively, if the test signals do not match the test tones by more than a predetermined variance, then the validation test result can be a fail. When the variance is so great that compensation cannot be effectively provided, then the user may be instructed to replace the incompatible listening device 110 with a compatible listening device 110 at operation 2412.

In the case of a marginal pass, e.g., when the test signals match the test tones within a certain range less than a range that indicates a close match but more than incompatible amount, the health sound recorder application 2012 can make setting changes to an audio equalizer function in the health sound recorder application 2012, at operation 2414. More particularly, the health sound recorder application 2012 can determine, based on the comparison between the test signals and the test tones, an equalization filter to compensate for a frequency response of the listening device 110. The equalization filter can correct a non-linearity of the frequency response of the listening device 110. More particularly, when the equalization filter is applied to audio data corresponding to sounds detected by the listening device 110, the modified audio data produces a linear frequency response for the earphone 600. The health sound recorder application 2012 can therefore tune the system to achieve a very flat/true frequency response over the audible frequency range. Accordingly, the listening device 110 can be validated for generating audio data that accurately and consistently represents sounds from the target anatomy.

The validation operation can be required prior to performing any self-auscultation recording. After exiting the health sound recorder application 2012, when the user returns to, e.g., re-launches, the application, the application can provide the user the option to go directly to the first sub-operation in the validation procedure to re-validate the self-auscultation device 102 and confirm it is still capable of providing an acceptable linear frequency response across the audible spectrum.

Referring again to FIG. 21, when the setup, system configuration, and system validation operations are complete, the self-auscultation system can be used to self-auscultate a target anatomy. A remote patient 104 can use the self-auscultation system to record audio data from the target anatomy, and to share the audio data with their healthcare provider 106 for further evaluation and monitoring.

At operation 2108, the patient 104 can use the self-auscultation system to record sounds from the target anatomy. The patient 104 can hold the self-auscultation device 102 to their chest and initiate a monitoring session through the health sound recorder application 2012. When the session is initiated, e.g., by pressing "start recording," the listening device 110 can detect sounds from the target anatomy that are conducted through the chest piece 202 and/or adaptor 204 to the microphone 206. The listening device 110 can generate audio data corresponding to the sounds. The listening device 110 can transmit the audio data to the health sound recorder application 2012 on the mobile device 108 via a wireless communication link. The health sound recorder application 2012 can then create an auscultation audio data file that contains the audio data along with specific reference parameters such as a patient ID code and the date and time of the recording. More specifically, these reference parameters for each auscultation audio data file can be contained in metadata, also referred to as coded tone sequences, that are prepended and post pended to the recorded audio data. The metadata can include segments, e.g., segment headers or segment trailers, that include metadata sequences prepended and/or post pended to the audio data. For example, the metadata sequences can include sequences of coded tones that represent information about the audio data recording. The metadata can include the patient ID code, date and time, contact point, A/D sampling rate, equalization file name, duration of audio data recording. The metadata may be any of several metadata types, including descriptive metadata (e.g., which contact point on the chest is being monitored), structural metadata (e.g., a length of the recording in seconds), administrative metadata (e.g., the data and time of the recording), or reference metadata (e.g., the serial number of the chest piece).

At operation 2109, the audio data can be transmitted from the mobile device 108 to a data processing system. For example, the audio data (raw or modified) can be transmitted from the mobile device 108 to the healthcare provider (to the healthcare provider device 112 or the remote server 114) via the mobile device 108. The healthcare provider 106 may further process and/or modify the audio data as described below. Alternatively, if there is no immediate need to transmit the auscultation audio data, or if there is no access to a communication link, the health sound recorder application 2012 on the mobile device 108 can process and/or modify the audio data as described below.

At operation 2110, the audio data files can be processed and/or reviewed. In an embodiment, the equalization filter determined during the validation procedure is applied to the audio data generated by the listening device 110. The equalization filter can be applied at the mobile device 108, e.g., when the mobile device is performing comparisons between the recorded audio data and predetermined auscultation audio data, as described below. Alternatively, the equalization filter can be applied at the healthcare provider 106 when the healthcare provider does not intend for the patient 104 to have access to health condition information without the consultation of a physician.

The health sound recorder application 2012 running on the patient or healthcare provider data processing systems can access a library collection of audio sound files of known auscultation audio data from both healthy patients and sick patients. In an embodiment, remote health monitoring system 100 can compare the audio data generated by the self-auscultation device 102 to the predetermined auscultation audio data. The comparison can be between frequency content of the recorded auscultation audio data from the remote patient 104 and frequency content of the auscultation audio data in the library. Based on the comparison, the data processing system performing the comparison can determine whether the sound matches the predetermined auscultation sound.

The data processing system(s) can use the self-auscultation frequency analysis algorithms 2016 to perform the comparison. The health sound recorder application 2012 identifies and extracts the most relevant sub-segments of the recorded auscultation audio for further analysis. The sub-segment data is then subjected to an analysis that determines the spectral frequency content of each relevant sub-segment of recorded audio data. The self-auscultation frequency analysis algorithms 2016 can utilize the Fast Fourier Transform to extract the spectral frequency content of an audio signal.

The self-auscultation frequency analysis algorithms 2016 can read metadata, e.g., coded tone sequences, in each audio data file to know additional details about the recording, such as what contact point was being monitored and/or date and time of the recording. The coded tone sequences include audio data corresponding to sound, and the audio data includes a first segment of coded tones at a beginning of the audio data and a second segment of coded tones at an end of the audio data. The self-auscultation frequency analysis algorithms 2016 will maintain the information contained in the coded tone sequences by including that metadata information prepended and post pended to the frequency analysis results. The specific parameters contained in the coded tone sequences enable the automated audio analysis software to perform relevant comparisons of audio files by knowing exactly which predetermined audio data to use in the comparison.

In an embodiment, after processing the auscultation audio data through the self-auscultation frequency analysis algorithms 2016, the health sound recorder application 2012 can save the results in a self-auscultation frequency analysis data file 2018. The frequency analysis data file 2018 can then be compared to the library of frequency content patterns in an effort to determine a diagnosis based on identifying a match.

The library of audio data files 2020 stored in the memory of the various data processing systems of the remote health monitoring system 100 contains a collection of auscultation sounds from various health conditions. More particularly, the library contains audio data files representing the sounds (and corresponding frequency content) of known auscultation data from both healthy patients and sick patients. In an embodiment, the health sound recorder application 2012 determines, based on the comparison (e.g., whether the recorded and predetermined sound match) whether the sound from the self-auscultation of the target anatomy indicates a health condition. More particularly, the application can isolate a match between the sounds emitted by the target anatomy of the self-isolated patient 104, and the sounds emitted by the target anatomy of other individuals having known health conditions (e.g., pneumonia, caused by a COVID-19 viral infection) to determine whether the self-isolated patient 104 has any such health condition.

Review of audio data files can also be between historical measurements of the same patient 104. For example, self-auscultation audio data files 2014 can be created by the health sound recorder application 2012 each time the user runs a self-auscultation test. The self-auscultation audio data files 2014 can be stored in the memory of the various data processing systems of the remote health monitoring system 100. In an embodiment, the audio data from the self-auscultation device 102 can be compared to the self-auscultation audio data files 2014 stored over time to monitor a progression of the self-isolated patient 104. The comparison of the current audio data to historical audio data may detect audio patterns that suggest a deteriorating health condition.

When the health sound recorder application 2012 determines either that the generated audio data matches a known health condition, or that the health condition of the patient 104 is deteriorating, then an action can be taken. For example, the health sound recorder application 2012 can display, to the patient and/or the healthcare provider, that the recorded sounds indicate a particular health condition or health trend. Accordingly, the patient 104 can schedule a medical appointment and/or the healthcare provider 106 can contact the patient 104 to request such a medical appointment, when needed. Accordingly, the remote health monitoring system 100 allows the patient 104 with a contagious respiratory viral infection (e.g., COVID-19) to self-isolate in their residence while having vital access to the medical care needed to monitor for potential deterioration in their health condition.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An adaptor for a self-auscultation device, comprising:
    an adaptor wall extending around an adaptor channel, wherein the adaptor channel extends along a longitudinal axis through the adaptor, and wherein the adaptor channel is configured to conform to a listening device; and
    a seal mounted within the adaptor channel, wherein the seal extends around the longitudinal axis such that, when the listening device is inserted into the adaptor channel along the longitudinal axis, the seal is compressed between the adaptor wall and the listening device to form a seal between the adaptor and the listening device.

2. The adaptor of claim 1 further comprising a magnet coupled to the adaptor wall.

3. The adaptor of claim 1, wherein an outer surface of the adaptor wall is at least partly tapered.

4. The adaptor of claim 3, wherein the outer surface has an outer profile including a tapered segment.

5. The adaptor of claim 4, wherein the outer profile includes one or more cylindrical segments.

6. The adaptor of claim 1, further comprising an adaptor seal mounted on an outer surface of the adaptor wall.

7. An adaptor for a self-auscultation device, comprising:
    a first adaptor portion having a first channel portion; and
    a second adaptor portion having a second channel portion, wherein the first adaptor portion and the second adaptor portion are opposable and moveable relative to each other to form an adaptor channel from the first channel portion and the second channel portion, and wherein the adaptor channel is configured to conform to an outer surface of a listening device.

8. The adaptor of claim 7, wherein the first adaptor portion and the second adaptor portion have a same shape.

9. The adaptor of claim 7 further comprising a magnet coupled to the first adaptor portion or the second adaptor portion.

10. The adaptor of claim 7, wherein respective outer surfaces of the first adaptor portion and the second adaptor portion are at least partly tapered.

11. The adaptor of claim 10, wherein, when the adaptor portions are opposed, the respective outer surfaces have an outer profile including a tapered segment.

12. The adaptor of claim 11, wherein the outer profile includes one or more cylindrical segments.

13. An adaptor for a self-auscultation device, comprising:
    an adaptor wall extending around an adaptor channel, wherein the adaptor channel extends along a longitudinal axis through the adaptor, and wherein the adaptor channel is configured to conform to a listening device; and
    a cap mounted on the adaptor wall, wherein the cap is movable from an open state to a closed state, and wherein the longitudinal axis intersects the cap in the closed state.

14. The adaptor of claim 13, wherein the cap is hinged to the adaptor wall.

15. The adaptor of claim 13 further comprising a seal mounted within the adaptor channel to form a seal between the adaptor and the listening device.

16. The adaptor of claim 13, wherein a magnet is coupled to the adaptor wall.

17. The adaptor of claim 13, wherein an outer surface of the adaptor wall is at least partly tapered.

18. The adaptor of claim 17, wherein the outer surface has an outer profile including a tapered segment.

19. The adaptor of claim 18, wherein the outer profile includes one or more cylindrical segments.

20. The adaptor of claim 13, further comprising an adaptor seal mounted on an outer surface of the adaptor wall.

* * * * *